US006228583B1

(12) United States Patent
Guarente et al.

(10) Patent No.: US 6,228,583 B1
(45) Date of Patent: May 8, 2001

(54) ASSAYS FOR COMPOUNDS WHICH EXTEND LIFE SPAN

(75) Inventors: Leonard P. Guarente, Chestnut Hill; David A. Sinclair, Somerville, both of MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/127,670

(22) Filed: Jul. 31, 1998

Related U.S. Application Data
(60) Provisional application No. 60/054,629, filed on Aug. 4, 1997.

(51) Int. Cl.[7] ................................................ C12Q 1/68
(52) U.S. Cl. ............................... 435/6; 435/477; 435/483
(58) Field of Search ................................. 435/6, 477, 483

(56) References Cited

U.S. PATENT DOCUMENTS 6,043,053    3/2000    Barnes et al. ...................... 435/69.1

FOREIGN PATENT DOCUMENTS

WO 91/00920    1/1991    (WO) .
WO 97/24435    7/1997    (WO) .

OTHER PUBLICATIONS

Gangloff, Serge, et al., "The Yeast Type I Topoisomerase Top3 Interacts with Sgs1, a DNA Helicase Homolog: a Potential Eukaryotic Reverse Gyrase", *Mol. Cell. Biol.*, 14(12):8391–8398 (1994).

Christman, Michael F., et al., "Mitotic Recombination in the rDNA of *S. cerevisiae* is Suppressed by the Combined Action of DNA Topoisomerases I and II", *Cell*, 55:413–425 (1988).

Watt, Paul M., et al., "SGS1, a Homologue of the Bloom's and Werner's Syndrome Genes, Is Required for Maintenance of Genome Stability in *Saccharomyces cerevisiae*", *Genetics*, 144:935–945 (1996).

Watt, Paul M., et al., "Sgs1: A Eukaryotic Homolog of *E. coli* RecQ that Interacts with Topoisomerase II In Vivo and Is Required for Faithful Chromosome Segregation", *Cell*, 81:253–260 (1995).

Lu, Jian, et al., "Human Homologues of Yeast Helicase", *Nature*, 383:678–679 (1996).

Gottlieb, Shoshanna and Esposito, Rochelle E., "A New Role for a Yeast Transcriptional Silencer Gene, *SIR2*, in Regulation of Recombination in Ribosomal DNA", *Cell*, 56:771–776 (1989).

Kennedy, Brian K., et al., "Redistribution of Silencing Proteins from Telomeres to the Nucleolus is Associated with Extension of Life Span in *S. cerevisiae*", *Cell*, 89:381–391 (1997).

de Beus, Elizabeth, et al., "Yeast NOP2 Encodes an Essential Nucleolar Protein with Homology to a Human Proliferation Marker", *J. Cell Biol.*, 127:1799–1813 (1994).

Kadowaki, Tatsuhiko, et al., "Nuclear mRNA Accumulation Causes Nucleolar Fragmentation in Yeast mtr2 Mutant", *Mol. Biol. Cell*, 5:1253–1263 (1994).

Tani, Tokio, et al., "Nucleolar Accumulation of Poly (A)[+] RNA in Heat–shocked Yeast Cells: Implication of Nucleolar Involvement in mRNA Transport", *Mol. Biol. Cell*, 6:1515–1534 (1995).

Oates, Melanie, et al., "Structural Alterations of the Nucleolus in Mutants of *Saccharomyces cerevisiae* Defective in RNA Polymerase I", *Mol. Cell. Biol.*, 13(4):2441–2455 (1993).

Warner, Jonathan R., "Synthesis of Ribosomes in *Saccharomyces cerevisiae*", *Micro. Rev.*, 53(2) :256–271 (1989).

Kim, Raymond A. and Wang, James C., "A Subthreshold Level of DNA Topoisomerases Leads to the Excision of Yeast rDNA as Extrachromosomal Rings", *Cell*, 57:975–985 (1989).

Miller, Charles A. and Kowalski, David, "cis–Acting Components in the Replication Origin from Ribosomal DNA of *Saccharomyces cerevisiae*", *Mol. Cell. Biol.*, 13(9):5360–5369 (1993).

Nierras, Concepcion R., et al., "Does Saccharomyces need an Organized Nucleolus?", *Chromosoma*, 105:444–451 (1997).

Palladino, F., et al., "SIR3 and SIR4 Proteins are Required for the Positioning and Integrity of Yeast Telomeres", *Cell*, 75:543–555 (1993).

Holm, Connie, "Clonal Lethality Caused by the Yeast Plasmid $2\mu$ DNA", *Cell*, 29:585–594 (1982).

Sweeny, Rosemary and Zakian, Virginia A., "Extrachromosomal Elements Cause a Reduced Division Potential nib1 Strains of *Saccharomyces cerevisiae*", *Genetics*, 122:749–757 (1989).

Jamet–Vierny, Corinne, et al., "Senescence in Podospora anserina: Amplification of a Mitochondrial DNA Sequence", *Cell*, 21:189–194 (1980).

(List continued on next page.)

*Primary Examiner*—James Ketter
(74) *Attorney, Agent, or Firm*—Hamilton, Brook, Smith & Reynolds, P.C.

(57) ABSTRACT

Methods of identifying agents or compounds which are capable of inhibiting the replication and/or accumulation of DNA circles in cells are described. Also described are methods of assessing the ability of a compound to extend life span, as well as methods of extending life span, comprising administering to a cell a compound identified by the assays described herein which extends life span. The invention also pertains to isolated mWRN, or an active derivative or fragment thereof and to an isolated nucleic acid molecule which encodes mWRN, or an active derivative or fragment thereof.

13 Claims, 12 Drawing Sheets

OTHER PUBLICATIONS

Imamura, Osamu, et al., "Cloning of a Mouse Homologue of the Human Werner Syndrome Gene and Assignment to 8A4 by Fluorescence in Situ Hybridization", *Genomics*, 41:298–300 (1997).

Sinclair, D. A., et al., "Molecular Mechanisms of Yeast Aging", *TIBS*, 23:131–134 (1998).

Yu, C–E., et al., "Positional Cloning of the Werner's Syndrome Gene", *Science*, 272(5259) :258–262 (1996).

Lombard, D. B., et al., "Cloning the Gene for Werner Syndrome: A Disease with Many Symptoms of Premature Aging", *Trends in Genetics*, 12(8) :283–288 (1996).

Sinclair, D. A., et al., "Extrachromosomal rDNA Circles—A Cause of Aging in Yeast", *Cell*, 91:1033–1042 (1997).

Abstract from *Derwent Publications Ltd.*, Section Ch, Week 9832 (Japan No. JP–10–146188 A, issued Jun. 2, 1998).

```
-228    CCTGTGCGCCCCTTGGTATAAAGTTAGTAAATGTGAGGCCTGTCTCGAGG
        GCCTGTGCGCCCCTTGGTATAAAGTTAGTAAATGTGAGGCCTGTCTCGAGTCC
        TCCATAAATCATCCTGCTGGAGGAGACCCTTAGATCTGGCTCTTCAGGGGCATTTTAAAGACAAATGAAAATAAA
1/1
ATG GAA ACC ACT TCA CTA CAG CGG AAA TTT CCA GAA TGG ATG TCT ATG CAG AGT CAA AGA
 M   E   T   T   S   L   Q   R   K   F   P   E   W   M   S   M   Q   S   Q   R
61/21
TGT GCT ACA GAA AAG GCC TGC GTT CAG AAG AGT GTT CTT GAA GAT AAT CTC CCA TTC
 C   A   T   E   K   A   C   V   Q   K   S   V   L   E   D   N   L   P   F
121/41
TTA GAA TTC CCT GGA TCC ATT GTT TAC AGT GCT AGT GAT TGC AGT GAT TGC TCC TTC CTG TCT
 L   E   F   P   G   S   I   V   Y   S   A   S   D   C   S   F   L   S
181/61
GAA GAC ATT AGC ATG CGT CTG TCT GAT GGC GTG GTG GTG TTT GAC ATG GAA TGG CCG
 E   D   I   S   M   R   L   S   D   G   V   V   G   F   D   M   E   W   P
241/81
CCC ATA TAC AAG CCA GGG AAA CGA AGC ATT TCT TCC GTC ATC CAG TTC CCC CAG TTA AAA ATG
 P   I   Y   K   P   G   K   R   S   I   S   S   V   I   Q   F   P   Q   L   K   M
301/101
AAC AAA TGT TAC TTG TTT CAC ATT AAG AAG GCA TCA GTT TCA ATG GGG ATT GAA GGG GAC CAG TGG AAA ATG
 N   K   C   Y   L   F   H   I   K   K   A   S   M   G   I   E   G   D   Q   W   K   M
361/121
TTA CTA GAA AAC TCA ATT AAG AAG TTG GAG GTT GTG GAG CTG ACG GAT GTT GCC AAT
 L   L   E   N   S   I   K   K   L   E   V   V   E   L   T   D   V   A   N
421/141
CTT CTG CGT GAT TTT GAC GTC AAG AGT TTT GTG GAG
 L   L   R   D   F   D   V   K   S   F   V   E
451/151
```

FIG. 4A

```
481/161
GAA AAG TTG AAG TGC GCA GAG ACC TGG AGC CTC AAT GGT CTG GTT AAA CAC GTC TTA GGG
 E   K   L   K   C   A   E   T   W   S   L   N   G   L   V   K   H   V   L   G

541/181
AAA CAA CTT TTG AAA GAC AAG TCC ATC CGC TGC AGC AAT TGG AGT AAT TTC CCC CTC ACT
 K   Q   L   L   K   D   K   S   I   R   C   S   N   W   S   N   F   P   L   T

601/201
GAG GAC CAG AAA CTG TAT GCA GCC ACT GAT GCT TAT GCT GGT CTT ATC TAT CAA AAA
 E   D   Q   K   L   Y   A   A   T   D   A   Y   A   G   L   I   Y   Q   K

661/221
TTA GGA AAT TTG GGT GAT ACT GTG CAA GTG CTA AAT AAA GCA GAG AGG GAT CTA GCC AAT
 L   G   N   L   G   D   T   V   Q   V   L   N   K   A   E   R   D   L   A   N

721/241
CCT CTG GAG ATG AAG AAA CAG TTG AAT TTA GAA GAA ATG AGG GTT CCT GTA ATA TTG AAG
 P   L   E   M   K   K   Q   L   N   L   E   E   M   R   V   P   V   I   L   K

781/261
CGT TTT CCT GTC ACT TGC AGA AAT CTC TGT TCA TTG GAA CAG AGG GGT CCT ACA AAC ACT GAG
 R   F   P   V   T   C   R   N   L   C   S   L   E   Q   R   G   P   T   N   T   E

841/281
AGT ATT TCA GAA AAT CTC TGT TCA TTG AGA AAT TTG TCA TTG AGA GAT TCA GCT GCT GCT
 S   I   S   E   N   L   C   S   L   R   N   L   S   L   R   D   S   A   A   A

901/301
ACT AGA CTG AAG CCG GGC AGT AGT TTT AAT CAT AAA CAG AGT ACT TTA CTG TCA TCA GCT GCT GCT
 T   R   L   K   P   G   S   S   F   N   H   K   Q   S   T   L   L   S   S   A   A   A

961/321
GGA GAA AAA GAG AAA CAG ATT GGA AAA CAT TTT GCT AAA ATT AAA GAA GAA CCA
 G   E   K   E   K   Q   I   G   K   H   F   A   K   I   K   E   E   P

991/331
AGT ACT TTT
 S   T   F

FIG. 4B
```

```
1021/341
TGG GAC CCA GAA CTT GAC AGT TTA GTG AAG GAG GAT GTA TTT AGA AAT CAA
 W   D   P   E   L   D   S   L   V   K   E   D   V   F   R   N   Q

1081/361
GTG AAG CAA GAA AAA GGT GAA TCT GAA AAT ATA GAA GAT CTG TTG AGA GAA GAT
 V   K   Q   E   K   G   E   S   E   N   I   E   D   L   L   R   E   D

1141/381
ATG GAA AGA ACT TGT GTG ATT CCT AGT ATT TCA GAA AAT GAA CTC CAA GAT TTG GAA CAG
 M   E   R   T   C   V   I   P   S   I   S   E   N   E   L   Q   D   L   E   Q

1201/401
CAA GCT AAA GAA GAA AAA TAT AAT GAT GTT TCT CAC CAA CTT TCT GAG CAT TTA TCT CCC
 Q   A   K   E   E   K   Y   N   D   V   S   H   Q   L   S   E   H   L   S   P

1261/421
AAT GAT GAG AAT GAC TCC TCC TAT ATA ATT GAA AGT GAT GAA GAT TTG GAA ATG GAG
 N   D   E   N   D   S   S   Y   I   I   E   S   D   E   D   L   E   M   E

1321/441
ATG CTG AAG TCT TTA GAA AAC CTA AAT AGT GAC ATG GTG GAA CCC ACT CAC TCT AAA TGG
 M   L   K   S   L   E   N   L   N   S   D   M   V   E   P   T   H   S   K   W

1381/461
TTG GAA ATG GGA TGT CTT CCT GAG GAG GAA GAT GGA CAC GGA AAT GAA
 L   E   M   G   C   L   P   E   E   E   D   G   H   G   N   E

1441/481
GCC ATC AAA GAG GAG CAG CAT TTA TTG CCG GAA CCC AAC GCA AAG CAA
 A   I   K   E   E   Q   H   L   L   P   E   P   N   A   K   Q

1501/501
ATT AAT TGC CTC AAG ACC TAT TTC GGA CAC AGT TTT AAA CCG GTT CAG TGG AAA GTC
 I   N   C   L   K   T   Y   F   G   H   S   F   K   P   V   Q   W   K   V

1531/511
AGC AGT TTT
 S   S   F
```

FIG. 4C

```
1561/521
ATC CAT TCT GTA TTA GAA GAG AGA GAT                     1591/531
 I   H   S   V   L   E   E   R   D                 AAT GTT GTC ATG GCA ACT GGA TAT GGG
                                                     N   V   V   M   A   T   G   Y   G
1621/541
AAG AGT CTG TGC TTC CAG TAT CCG CCT GTT                 1651/551
 K   S   L   C   F   Q   Y   P   P   V             TAT ACA GGC AAG ATT GTC ATT TCA
                                                     Y   T   G   K   I   V   I   S
1681/561
CCT CTC ATT TCC TTA ATG GAA GAC CAA GTC                 1711/571
 P   L   I   S   L   M   E   D   Q   V             CTC CAG CTT GAG CTA TCC AAT GTT CCA GCC
                                                     L   Q   L   E   L   S   N   V   P   A
1741/581
TGT TTA CTT GGA TCT GCA CAA TCA AAA AAT                 1771/591
 C   L   L   G   S   A   Q   S   K   N             ATT CTA GGA GAT GTT AAA TTA GGC AAA TAT
                                                     I   L   G   D   V   K   L   G   K   Y
1801/601
AGG GTC ATC TAC ATA ACT CCA GAG TTC TGT                 1831/611
 R   V   I   Y   I   T   P   E   F   C             TCT GGT AAC TTG GAT CTA CTC CAG AAA CTT
                                                     S   G   N   L   D   L   L   Q   K   L
1861/621
GAC TCT AGT ATT GGC ATC ACT CTC ATT GCT                 1891/631
 D   S   S   I   G   I   T   L   I   A             GTG GAT GAG GCT CAC TGC ATT TCA GAG TGG
                                                     V   D   E   A   H   C   I   S   E   W
1921/641
GGC CAT GAT TTC AGA AGT TCA TTC AGG ATG                 1951/651
 G   H   D   F   R   S   S   F   R   M             CTG GGC TCT CTT AAA ACA GCG CTC CCA TTG
                                                     L   G   S   L   K   T   A   L   P   L
1981/661
GTT CCA GTC ATT GCA CTC TCC GCT ACT GCA                 2011/671
 V   P   V   I   A   L   S   A   T   A             AGC TCT TCC ATC CGG GAA GAC ATT ATA AGC
                                                     S   S   S   I   R   E   D   I   I   S
2041/681
TGC TTA AAC CTG AAA GAC CCT CAG ATC ACC                 2071/691
 C   L   N   L   K   D   P   Q   I   T             TGC ACT GGA TTT GAT CGG CCA AAT CTG TAC
                                                     C   T   G   F   D   R   P   N   L   Y
```

```
2641/881
CAT TTT GAG GAC AAA TGT CTG CAG AAG GCC ATT ATG GGA ACT GAA AAA TGC
 H   F   E   D   K   C   L   Q   K   A   I   M   G   T   E   K   C

2701/901
TGT GAT AAT TGC AGG CCC AGG CTG AAT CAT TTC ACT GCT AAC TCA GAG GAC GCA
 C   D   N   C   R   P   R   L   N   H   F   T   A   N   S   E   D   A

2761/921
TCC CAA GAC TTT GGG CCA CAA GCA TTC CAG CTA CTG TCT GCT GTG GAC ATC CTG CAG GAG
 S   Q   D   F   G   P   Q   A   F   Q   L   L   S   A   V   D   I   L   Q   E

2821/941
AAA TTT GGA ATT GGG ATT CCG ATC TTA TTT CTC CGA GGA TCT AAT TCT CAG CGT CTT CCT
 K   F   G   I   G   I   P   I   L   F   L   R   G   S   N   S   Q   R   L   P

2881/961
GAT AAA TAT CGG GGT CAC AGG CTC TTT GGT ATA GCT GAA CAA GCA GAA AGT TGG TGG
 D   K   Y   R   G   H   R   L   F   G   I   A   E   Q   A   E   S   W   W

2941/981
AAG ACT CTT TCT CAC CAT CTC ATA GCT GAA AAA GAG TTC TTG GTA GAG GTT CCC AAG GAA AAC
 K   T   L   S   H   H   L   I   A   E   K   E   F   L   V   E   V   P   K   E   N

3001/1001
AAA TAT ATA AAG ACA TGT TCC CTT CTT CAA ACA AAA TGG CTT AGA ATG TTT CCA AGG AAA GTT
 K   Y   I   K   T   C   S   L   L   Q   T   K   W   L   R   M   F   P   R   K   V

3061/1021
TTG CAG TCT CCT CCG AGC CTT CTC CTT CAA GAG ATG AAT GAA CAA CAT TCC TCT AAT CAA AAC
 L   Q   S   P   P   S   L   L   L   Q   E   M   N   E   Q   H   S   S   N   Q   N

3121/1041
CTG CTA CCA AGT TCT AAT CCT GTA TCT CCA ACG CAA GAA ACG CAA CAT TCC TCT AAT CAA AAC
 L   L   P   S   S   N   P   V   S   P   T   Q   E   T   Q

3151/1051
CCA GTA TCT CCA ACG CAA GAA ACG
 P   V   S   P   T   Q   E   T
```

FIG. 4F

```
3181/1061
CCA GCT GGA TTA ACT ACC AAG CAG TCT AAT TTG GAG AGA ACG CAT TCT TAC AAA GTG CCT
 P   A   G   L   T   T   K   Q   S   N   L   E   R   T   H   S   Y   K   V   P

3241/1081
GAG AAA GTT TCT TCT GGG ACT AAC ATT CCT AAA AAA AGT GCC GTG ATG CCG TCA CCA GGA
 E   K   V   S   S   G   T   N   I   P   K   K   S   A   V   M   P   S   P   G

3301/1101
ACA TCT TCC AGC CCC TTA GAA CCT GCC ATC TCA GCC CAA GAG CTG GAC GCT CGG ACT GGG
 T   S   S   S   P   L   E   P   A   I   S   A   Q   E   L   D   A   R   T   G

3361/1121
CTA TAT GCC AGG TTG GTG GAA GCA AGG CAG AAT AAG CAC GCT AAG ATG GAT GTA CCT CCA
 L   Y   A   R   L   V   E   A   R   Q   N   K   H   A   K   M   D   V   P   P

3421/1141
GCT ATT TTA GCA ACA AAC AAG GTT CTG CTG TCT CAA GTA AAA ATG GCT AGA CCG ACT GTT
 A   I   L   A   T   N   K   V   L   L   S   Q   V   K   M   A   R   P   T   V

3481/1161
GAA AAC ATG AAA CAG ATC GAC GGT GTC TCT AAA AGT GAA GGC AAA GCT GCT CTG TTG GCC CCT CTG
 E   N   M   K   Q   I   D   G   V   S   K   S   E   G   K   A   A   L   L   A   P   L

3541/1181
TTG GGA GTC ATC AAA CAT TTC TGT CAA GTA CAG AGT GTT CAG ACA GAC CTC CTT TCC AGT
 L   G   V   I   K   H   F   C   Q   V   Q   S   V   Q   T   D   L   L   S   S

3601/1201
GCC AAA CCT CAC AAG GAA CAG GAG ATG AAA AGT CAG GAG ATG GAA AAG AAA GAC TGC TCA CTC
 A   K   P   H   K   E   Q   E   M   K   S   Q   E   M   E   K   K   D   C   S   L

3661/1221
CCC CAG TCT GTG GCC ACA TAC ACT CTA TTC CAG GAA AAG AAA ATG CCC TTA CAC AGC
 P   Q   S   V   A   T   Y   T   L   F   Q   E   K   K   M   P   L   H   S
```

FIG. 4G

```
3721/1241
ATA GCT GAG AAC AGG CTC CTG CCT CTC ACA
I   A   E   N   R   L   L   P   L   T

3751/1251
                                        GCA GTC GGC ATG CAC TTA GCC CAG GCG GTG
                                        A   V   G   M   H   L   A   Q   A   V

3781/1261
AAA GCC GGC TAC CCC CTG GAT ATG GAG CGA GCT GGC CTG ACC CCA GAG ACT TGG AAG ATT
K   A   G   Y   P   L   D   M   E   R   A   G   L   T   P   E   T   W   K   I

3841/1281
ATT ATG GAT GTC ATC CGA AAC CCT CCC ATC AAC TCA GAT ATG TAT AAA GTT AAA CTC ATC
I   M   D   V   I   R   N   P   P   I   N   S   D   M   Y   K   V   K   L   I

3901/1301
AGA ATG TTA GTT CCT GAA AAC ATC GAC ACG TAC CTC ATC CAC ATG GCG ATT GAG ATT CTT
R   M   L   V   P   E   N   I   D   T   Y   L   I   H   M   A   I   E   I   L

3961/1321
CAG AGT GGT TCC GAC AGC AGA ACC CAG CCT TGT GAT TCC AGC AGG AAG AGG CGT TTC
Q   S   G   S   D   S   R   T   Q   P   C   D   S   S   R   K   R   R   F

3991/1331
                                        CCT TGT GAT TCC AGC AGG AAG AGG CGT TTC
                                        P   C   D   S   S   R   K   R   R   F

4021/1341
CCC AGC TCT GCA GAG TGT GAG AGT TGT GAG AGC TGT AAA GAG AGC AAA GAG GTG GTC ACC GAG ACC
P   S   S   A   E   C   E   S   C   E   S   C   K   E   S   K   E   V   V   T   E   T

4051/1351
                                        AAG GAG AGC AAA GAG TGG TTT GCC AAA GGA AAT GTG
                                        K   E   S   K   E   W   F   A   K   G   N   V

4081/1361
AAG GCA TCA TCT TCA GAG TCA AAG AGA AAA TTA CCT GAG TGG TTT GCC AAA GGA AAT GTG
K   A   S   S   S   E   S   K   R   K   L   P   E   W   F   A   K   G   N   V

4111/1371
                                        TTA CCT GAG TGG TTT GCC AAA GGA AAT GTG
                                        L   P   E   W   F   A   K   G   N   V

4141/1381
CCC TCA GCT GAT ACC GGC AGC TCA TCA TCA TCA TCA TCA AAA AAG AAA GGT CTC TTT
P   S   A   D   T   G   S   S   S   S   S   S   K   K   K   G   L   F

4171/1391
                                        ATG GCC AAG AAA AAG ACC GAG AAT GTG
                                        M   A   K   K   K   T   E   N   V
```

FIG. 4H

4201/1401
AGT TAA GATGACAACGATGGAACAGTTTGTGTGTCCTACATCTTCATTCCTATAAAGAATGAAAAGAAATATTTAAC
S  *
GATGACAACGATGGAACAGTTTGTGTGTCCTACATCTTCATTCCTATAAAGAATGAAAAGAAATATTTAACCTCAAAAT
TATTTAAGTCCAAAGTGAAGCTCACCTAAACGTCGAGCCATAGAGTCTTTAATTGCCCGTTGGCAGTTGAGCTACAGTA
TCTGAACCTTCTGAGACCCGAGTGCAGCATAGACTGTGAAGTCGGCTTCCTTTCCGATTGCCTTCCGAACCGGTGCCAC
TGTCAGGTTGCAGTCTTTCTCTTGCAGCAGTGTGTTGGAAATGGAGGCTGTCGCTTTGACATATAGAACAGAT
CAATAGTTGCATAGGGACAGATGAAGATACAGCCGGTCTTTGCTTTCTTATGCAGATGCCTGTATGACAGTATCAGTG
CACCAGCCCAGGAGGACATCAGCTTCCATTTAAAAAGGGAAAGCGGACAAGGACTCCAGTTACAGAAACAACTAAA
TTCTATGCATTTCTGCAGTCTTTATTATTTCAATATTTGAAGATGCCAATTTTGAAGTGTTCTTTGTACTGAATAGTAAATATACTAAATTTTC
ATTTTTAAATTGTTGTGAGTCTGTTCTTTTTTTGGTAAATAGAACTATTGTTATATAAACTGTAAACTCTGTTCTTTTTTTTGGTAAATAGAACTATTGTTATATAAATGGACTGTTATTAATGTAGGAAAAATACACCTGAATTCAGAGAAGTT
ACTGAAAATTCAACTCTGTTCTTTTTTTGGTAAATAGAACTATTGTTATATAAATGGACTGTTATTAATGTAGGAAAAATACACCTGAATTCAGAGAAGTT
GCCTTGATTAACTTTTTTTGGTAAATAGAACTATTGTTATATAAATGGACTGTTATTAATGTAGGAAAAATACACCTGAATTCAGAGAAGTT
AAAAAAGTCACTCAGGGTTCCATTATATAAGACATTCAAATCAAACTATAATTAAAACATAGAAACTTCTCTGTGCCTTAAACTGTGTCTATA
TTTTCTTAATTTGAATCTTATTATAAGACATTCACGCATAATCTCCAGTGCTCCCTGCCTGGTTCAGCGCTCAGTGGTTTTCAGCCTGGGAATTGAAAAACAAAGCTTGGGGCAAAA
ATTACCAGAAGGTAGCTTGTATTCTCGTGGCAGTAGTTGAACTGGTTGTTATTTGGCAGACATTTCAAGACATTTCTAGCAAAATTACAATTCTGTGAACAGGTGTCCTTC
ATGCATGAGGTGGTAGTTGTTTTGACTTATGAGTTGAACTGGTTGTTATTTGGCAGACATTTCAAGACATTTCTAGCAAAATTACAATTCTGTGAACAGGTGTCCTTC
TGCTTCATTGTTGGTTTTTAGACTTGTTATTTGCCAGTAATAAAATTGCACTGAGGGCTTTCTTCCTTGACCTGAGGGCTTTTCTAATGAGATGAATAAAATAAACACATTATTTTTGATAC
GTAAGCTTACCAATATTATTGCCAGTAATAAAATTGCACTGAGGGCTTTCTTCCTTGACCTGAGGGCTTTTCTAATGAGATGAATAAAATAAACACATTATTTTTGATAC
ATGACTTACCAATATTATTGCCAGTAATAAAATTGCACTGAGGGCTTTCTTCCTTGACCTGAGGGCTTTTCTAATGAGATGAATAAAATAAACACATTATTTTTGATAC
ACTGGGAGCCTGGGCAGCTTTCCTTGACCTGAGGGCTTTTCTAATGAGATGAATAAAATAAACACATTATTTTTGATAC
TATCTAAAGTTTCATCTGTATCTGGAACATCTAAGTGACCCAAGAAATCAGTGTTTAATGACAACTAAGACACGTTATA
ATATAGCATATATAGTTTCATTTCAAAGATTTAAAGTTTCAAAGATTCTGTACATTTGTACCAATTTGAAAAGTATTTCAAATAGCTT
ACAGCTACAGTTTCATTTCAAAGATTTAAAGTTTCAAAGATTCTGTACATTTGTAAAAGTATTTCAAATAGCTT
TCCTAATATAGCACACACACAACACACACAGAACACTGAATACAGTAGACCAGTAGACAGTAGACCAGTAGACTCCTTCTTC
TCCTGAACTCATCCACAACGAGAACATTTACAGAAATGAAATGGGGCCATCCTGTCTTTTTTAAATGTAAATGTG
ATTTAAAACGAACAATATTTGTCTAAATTGTAATTGTTACTGGCAGCCATTTTAAATGAATCAATAAATCTTTGA
AAAAGCCTCCAAAAAAAAAAAAAAAAAAAAAAAAAAAAAAAAAAAA
                                                                    6248

SEQUENCE LISTING

```
<160> NUMBER OF SEQ ID NOS: 6

<210> SEQ ID NO 1
<211> LENGTH: 33
<212> TYPE: DNA
<213> ORGANISM: Artificial Sequence
<220> FEATURE:
<223> OTHER INFORMATION: Synthetic oligonucleotide sequence

<400> SEQUENCE: 1 ggggggatc caattgtaga aatagcgcca acg                                  33

<210> SEQ ID NO 2
<211> LENGTH: 33
<212> TYPE: DNA
<213> ORGANISM: Artificial Sequence
<220> FEATURE:
<223> OTHER INFORMATION: Synthetic oligonucleotide sequence

<400> SEQUENCE: 2 gggggagct ctcactttct tcctctgtag tga                                  33

<210> SEQ ID NO 3
<211> LENGTH: 36
<212> TYPE: DNA
```

```
<213> ORGANISM: Artificial Sequence
<220> FEATURE:
<223> OTHER INFORMATION: Synthetic oligonucleotide sequence

<400> SEQUENCE: 3
gggggggatc cagtgacgaa gccgtcacat aactta                                    36

<210> SEQ ID NO 4
<211> LENGTH: 40
<212> TYPE: DNA
<213> ORGANISM: Artificial Sequence
<220> FEATURE:
<223> OTHER INFORMATION: Synthetic oligonucleotide sequence

<400> SEQUENCE: 4 gggggcggc cgcttatcac tttcttcctc tgtagtgacc                                 40

<210> SEQ ID NO 5
<211> LENGTH: 6476
<212> TYPE: DNA
<213> ORGANISM: Murine
<220> FEATURE:
<221> NAME/KEY: CDS
<222> LOCATION: (229)...(4432)

<400> SEQUENCE: 5
ccggaagggc aggcgccaga ccagaagtgc accgaggcgc ccgttggtat aaagttagta          60
aatgtgaggc ctgtgcgccc gttggtataa agttagtaaa tgtgaggcct gtctcgatgc         120
ctgggtcctg gcctttggtt ctcagtcctc cataaatcat cctgctggag agaagaccc          180 ttagatctgg ctcttctcag ggcattttta aagacaaatg aaaataaa atg gaa acc          237
                                                     Met Glu Thr
                                                       1
```

| | | | | | | | | | | | | | | | | |
|---|---|---|---|---|---|---|---|---|---|---|---|---|---|---|---|---|
| act | tca | cta | cag | cgg | aaa | ttt | cca | gaa | tgg | atg | tct | atg | cag | agt | caa | 285 |
| Thr | Ser | Leu | Gln | Arg | Lys | Phe | Pro | Glu | Trp | Met | Ser | Met | Gln | Ser | Gln | |
| | 5 | | | | 10 | | | | | 15 | | | | | | |
| aga | tgt | gct | aca | gaa | gaa | aag | gcc | tgc | gtt | cag | aag | agt | gtt | ctt | gaa | 333 |
| Arg | Cys | Ala | Thr | Glu | Glu | Lys | Ala | Cys | Val | Gln | Lys | Ser | Val | Leu | Glu | |
| 20 | | | | | 25 | | | | | 30 | | | | | 35 | |
| gat | aat | ctc | cca | ttc | tta | gaa | ttc | cct | gga | tcc | att | gtt | tac | agt | tat | 381 |
| Asp | Asn | Leu | Pro | Phe | Leu | Glu | Phe | Pro | Gly | Ser | Ile | Val | Tyr | Ser | Tyr | |
| | | | 40 | | | | | 45 | | | | | 50 | | | |
| gaa | gct | agt | gat | tgc | tcc | ttc | ctg | tct | gaa | gac | att | agc | atg | cgt | ctg | 429 |
| Glu | Ala | Ser | Asp | Cys | Ser | Phe | Leu | Ser | Glu | Asp | Ile | Ser | Met | Arg | Leu | |
| | | | 55 | | | | | 60 | | | | | 65 | | | |
| tct | gat | ggc | gat | gtg | gtg | gga | ttt | gac | atg | gaa | tgg | ccg | ccc | ata | tac | 477 |
| Ser | Asp | Gly | Asp | Val | Val | Gly | Phe | Asp | Met | Glu | Trp | Pro | Pro | Ile | Tyr | |
| | | 70 | | | | | 75 | | | | | 80 | | | | |
| aag | cca | ggg | aaa | cga | agc | aga | gtc | gca | gtg | atc | cag | ttg | tgt | gtg | tct | 525 |
| Lys | Pro | Gly | Lys | Arg | Ser | Arg | Val | Ala | Val | Ile | Gln | Leu | Cys | Val | Ser | |
| | 85 | | | | | 90 | | | | | 95 | | | | | |
| gag | aac | aaa | tgt | tac | ttg | ttt | cac | att | tct | tcc | atg | tca | gtt | ttc | ccc | 573 |
| Glu | Asn | Lys | Cys | Tyr | Leu | Phe | His | Ile | Ser | Ser | Met | Ser | Val | Phe | Pro | |
| 100 | | | | | 105 | | | | | 110 | | | | | 115 | |
| cag | gga | tta | aaa | atg | tta | cta | gaa | aac | aaa | tca | att | aag | aag | gca | ggg | 621 |
| Gln | Gly | Leu | Lys | Met | Leu | Leu | Glu | Asn | Lys | Ser | Ile | Lys | Lys | Ala | Gly | |
| | | | 120 | | | | | 125 | | | | | 130 | | | |
| gtt | ggg | att | gaa | ggg | gac | cag | tgg | aaa | ctt | ctg | cgt | gat | ttt | gac | gtc | 669 |
| Val | Gly | Ile | Glu | Gly | Asp | Gln | Trp | Lys | Leu | Leu | Arg | Asp | Phe | Asp | Val | |
| | | 135 | | | | | 140 | | | | | 145 | | | | |

```
aag ttg gag agt ttt gtg gag ctg acg gat gtt gcc aat gaa aag ttg       717
Lys Leu Glu Ser Phe Val Glu Leu Thr Asp Val Ala Asn Glu Lys Leu
            150                 155                 160 aag tgc gca gag acc tgg agc ctc aat ggt ctg gtt aaa cac gtc tta       765
Lys Cys Ala Glu Thr Trp Ser Leu Asn Gly Leu Val Lys His Val Leu
165                 170                 175 ggg aaa caa ctt ttg aaa gac aag tcc atc cgc tgc agc aat tgg agt       813
Gly Lys Gln Leu Leu Lys Asp Lys Ser Ile Arg Cys Ser Asn Trp Ser
180                 185                 190                 195 aat ttc ccc ctc act gag gac cag aaa ctg tat gca gcc act gat gct       861
Asn Phe Pro Leu Thr Glu Asp Gln Lys Leu Tyr Ala Ala Thr Asp Ala
                200                 205                 210 tat gct ggt ctt atc atc tat caa aaa tta gga aat ttg ggt gat act       909
Tyr Ala Gly Leu Ile Ile Tyr Gln Lys Leu Gly Asn Leu Gly Asp Thr
            215                 220                 225 gtg caa gtg ttt gct cta aat aaa gca gag gaa aac cta cct ctg gag       957
Val Gln Val Phe Ala Leu Asn Lys Ala Glu Glu Asn Leu Pro Leu Glu
        230                 235                 240 atg aag aaa cag ttg aat tta atc tcc gaa gaa atg agg gat cta gcc      1005
Met Lys Lys Gln Leu Asn Leu Ile Ser Glu Glu Met Arg Asp Leu Ala
245                 250                 255 aat cgt ttt cct gtc act tgc aga aat ttg gaa act ctc cag agg gtt      1053
Asn Arg Phe Pro Val Thr Cys Arg Asn Leu Glu Thr Leu Gln Arg Val
260                 265                 270                 275 cct gta ata ttg aag agt att tca gaa aat ctc tgt tca ttg aga aaa      1101
Pro Val Ile Leu Lys Ser Ile Ser Glu Asn Leu Cys Ser Leu Arg Lys
                280                 285                 290 gtg atc tgt ggt cct aca aac act gag act aga ctg aag ccg ggc agt      1149
Val Ile Cys Gly Pro Thr Asn Thr Glu Thr Arg Leu Lys Pro Gly Ser
            295                 300                 305 agt ttt aat tta ctg tca tca gag gat tca gct gct gct gga gaa aaa      1197
Ser Phe Asn Leu Leu Ser Ser Glu Asp Ser Ala Ala Ala Gly Glu Lys
        310                 315                 320 gag aaa cag att gga aaa cat agt act ttt gct aaa att aaa gaa gaa      1245
Glu Lys Gln Ile Gly Lys His Ser Thr Phe Ala Lys Ile Lys Glu Glu
325                 330                 335 cca tgg gac cca gaa ctt gac agt tta gtg aag caa gag gag gtt gat      1293
Pro Trp Asp Pro Glu Leu Asp Ser Leu Val Lys Gln Glu Glu Val Asp
340                 345                 350                 355 gta ttt aga aat caa gtg aag caa gaa aaa ggt gaa tct gaa aat gaa      1341
Val Phe Arg Asn Gln Val Lys Gln Glu Lys Gly Glu Ser Glu Asn Glu
                360                 365                 370 ata gaa gat aat ctg ttg aga gaa gat atg gaa aga act tgt gtg att      1389
Ile Glu Asp Asn Leu Leu Arg Glu Asp Met Glu Arg Thr Cys Val Ile
            375                 380                 385 cct agt att tca gaa aat gaa ctc caa gat ttg gaa cag caa gct aaa      1437
Pro Ser Ile Ser Glu Asn Glu Leu Gln Asp Leu Glu Gln Gln Ala Lys
        390                 395                 400 gaa gaa aaa tat aat gat gtt tct cac caa ctt tct gag cat tta tct      1485
Glu Glu Lys Tyr Asn Asp Val Ser His Gln Leu Ser Glu His Leu Ser
405                 410                 415 ccc aat gat gat gag aat gac tcc tcc tat ata att gaa agt gat gaa      1533
Pro Asn Asp Asp Glu Asn Asp Ser Ser Tyr Ile Ile Glu Ser Asp Glu
420                 425                 430                 435 gat ttg gaa atg gag atg ctg aag tct tta gaa aac cta aat agt gac      1581
Asp Leu Glu Met Glu Met Leu Lys Ser Leu Glu Asn Leu Asn Ser Asp
                440                 445                 450 atg gtg gaa ccc act cac tct aaa tgg ttg gaa atg gga acc aat ggg      1629
Met Val Glu Pro Thr His Ser Lys Trp Leu Glu Met Gly Thr Asn Gly
            455                 460                 465
```

```
tgt ctt cct cct gag gag gaa gat gga cac gga aat gaa gcc atc aaa      1677
Cys Leu Pro Pro Glu Glu Glu Asp Gly His Gly Asn Glu Ala Ile Lys
    470                 475                 480 gag gag cag gaa gaa gag gac cat tta ttg ccg gaa ccc aac gca aag      1725
Glu Glu Gln Glu Glu Glu Asp His Leu Leu Pro Glu Pro Asn Ala Lys
485                 490                 495 caa att aat tgc ctc aag acc tat ttc gga cac agc agt ttt aaa ccg      1773
Gln Ile Asn Cys Leu Lys Thr Tyr Phe Gly His Ser Ser Phe Lys Pro
500                 505                 510                 515 gtt cag tgg aaa gtc atc cat tct gta tta gaa gag aga aga gat aat      1821
Val Gln Trp Lys Val Ile His Ser Val Leu Glu Glu Arg Arg Asp Asn
            520                 525                 530 gtt gtt gtc atg gca act gga tat ggg aag agt ctg tgc ttc cag tat      1869
Val Val Val Met Ala Thr Gly Tyr Gly Lys Ser Leu Cys Phe Gln Tyr
            535                 540                 545 ccg cct gtt tat aca ggc aag att ggc att gtc att tca cct ctc att      1917
Pro Pro Val Tyr Thr Gly Lys Ile Gly Ile Val Ile Ser Pro Leu Ile
            550                 555                 560 tcc tta atg gaa gac caa gtc ctc cag ctt gag cta tcc aat gtt cca      1965
Ser Leu Met Glu Asp Gln Val Leu Gln Leu Glu Leu Ser Asn Val Pro
565                 570                 575 gcc tgt tta ctt gga tct gca caa tca aaa aat att cta gga gat gtt      2013
Ala Cys Leu Leu Gly Ser Ala Gln Ser Lys Asn Ile Leu Gly Asp Val
580                 585                 590                 595 aaa tta ggc aaa tat agg gtc atc tac ata act cca gag ttc tgt tct      2061
Lys Leu Gly Lys Tyr Arg Val Ile Tyr Ile Thr Pro Glu Phe Cys Ser
            600                 605                 610 ggt aac ttg gat cta ctc cag aaa ctt gac tct agt att ggc atc act      2109
Gly Asn Leu Asp Leu Leu Gln Lys Leu Asp Ser Ser Ile Gly Ile Thr
            615                 620                 625 ctc att gct gtg gat gag gct cac tgc att tca gag tgg ggc cat gat      2157
Leu Ile Ala Val Asp Glu Ala His Cys Ile Ser Glu Trp Gly His Asp
            630                 635                 640 ttc aga agt tca ttc agg atg ctg ggc tct ctt aaa aca gcg ctc cca      2205
Phe Arg Ser Ser Phe Arg Met Leu Gly Ser Leu Lys Thr Ala Leu Pro
    645                 650                 655 ttg gtt cca gtc att gca ctc tcc gct act gca agc tct tcc atc cgg      2253
Leu Val Pro Val Ile Ala Leu Ser Ala Thr Ala Ser Ser Ser Ile Arg
660                 665                 670                 675 gaa gac att ata agc tgc tta aac ctg aaa gac cct cag atc acc tgc      2301
Glu Asp Ile Ile Ser Cys Leu Asn Leu Lys Asp Pro Gln Ile Thr Cys
            680                 685                 690 act gga ttt gat cgg cca aat ctg tac tta gaa gtt gga cgg aaa aca      2349
Thr Gly Phe Asp Arg Pro Asn Leu Tyr Leu Glu Val Gly Arg Lys Thr
            695                 700                 705 ggg aac atc ctt cag gat cta aag ccg ttt ctc gtc cga aag gca agt      2397
Gly Asn Ile Leu Gln Asp Leu Lys Pro Phe Leu Val Arg Lys Ala Ser
            710                 715                 720 tct gcc tgg gaa ttt gaa ggt cca acc atc atc tat tgt cct tcg aga      2445
Ser Ala Trp Glu Phe Glu Gly Pro Thr Ile Ile Tyr Cys Pro Ser Arg
725                 730                 735 aaa atg aca gaa caa gtt act gct gaa ctt ggg aaa ctg aac tta gcc      2493
Lys Met Thr Glu Gln Val Thr Ala Glu Leu Gly Lys Leu Asn Leu Ala
740                 745                 750                 755 tgc aga aca tac cac gct ggc atg aaa att agc gaa agg aag gac gtt      2541
Cys Arg Thr Tyr His Ala Gly Met Lys Ile Ser Glu Arg Lys Asp Val
            760                 765                 770 cat cat agg ttc ctg aga gat gaa att cag tgt gtt gta gct act gta      2589
His His Arg Phe Leu Arg Asp Glu Ile Gln Cys Val Val Ala Thr Val
    775                 780                 785
```

```
gct ttt gga atg ggc att aat aaa gct gac att cgc aaa gtt att cat    2637
Ala Phe Gly Met Gly Ile Asn Lys Ala Asp Ile Arg Lys Val Ile His
        790                 795                 800 tat ggt gcg cct aag gaa atg gaa tcc tat tac cag gaa att ggt aga    2685
Tyr Gly Ala Pro Lys Glu Met Glu Ser Tyr Tyr Gln Glu Ile Gly Arg
805                 810                 815 gct ggc cgg gat gga ctt cag agt tcc tgt cac ttg ctc tgg gct cca    2733
Ala Gly Arg Asp Gly Leu Gln Ser Ser Cys His Leu Leu Trp Ala Pro
820                 825                 830                 835 gca gac ttt aac aca tcc agg aat ctc ctt att gag att cac gat gaa    2781
Ala Asp Phe Asn Thr Ser Arg Asn Leu Leu Ile Glu Ile His Asp Glu
            840                 845                 850 aag ttc cgg tta tat aaa tta aag atg atg gta aag atg gaa aaa tac    2829
Lys Phe Arg Leu Tyr Lys Leu Lys Met Met Val Lys Met Glu Lys Tyr
        855                 860                 865 ctt cac tcc agt cag tgt agg cga cga atc atc ttg tcc cat ttt gag    2877
Leu His Ser Ser Gln Cys Arg Arg Ile Ile Leu Ser His Phe Glu
        870                 875                 880 gac aaa tgt ctg cag aag gcc tcc ttg gac att atg gga act gaa aaa    2925
Asp Lys Cys Leu Gln Lys Ala Ser Leu Asp Ile Met Gly Thr Glu Lys
885                 890                 895 tgc tgt gat aat tgc agg ccc agg ctg aat cat tgc ctt act gct aac    2973
Cys Cys Asp Asn Cys Arg Pro Arg Leu Asn His Cys Leu Thr Ala Asn
900                 905                 910                 915 aac tca gag gac gca tcc caa gac ttt ggg cca caa gca ttc cag cta    3021
Asn Ser Glu Asp Ala Ser Gln Asp Phe Gly Pro Gln Ala Phe Gln Leu
            920                 925                 930 ctg tct gct gtg gac atc ctg cag gag aaa ttt gga att ggg att ccg    3069
Leu Ser Ala Val Asp Ile Leu Gln Glu Lys Phe Gly Ile Gly Ile Pro
        935                 940                 945 atc tta ttt ctc cga gga tct aat tct cag cgt ctt cct gat aaa tat    3117
Ile Leu Phe Leu Arg Gly Ser Asn Ser Gln Arg Leu Pro Asp Lys Tyr
        950                 955                 960 cgg ggt cac agg ctc ttt ggt gct gga aag gag caa gca gaa agt tgg    3165
Arg Gly His Arg Leu Phe Gly Ala Gly Lys Glu Gln Ala Glu Ser Trp
965                 970                 975 tgg aag act ctt tct cac cat ctc ata gct gaa gga ttc ttg gta gag    3213
Trp Lys Thr Leu Ser His His Leu Ile Ala Glu Gly Phe Leu Val Glu
980                 985                 990                 995 gtt ccc aag gaa aac aaa tat ata aag aca tgt tcc ctc aca aaa aag    3261
Val Pro Lys Glu Asn Lys Tyr Ile Lys Thr Cys Ser Leu Thr Lys Lys
            1000                1005                1010 ggt aga aag tgg ctt gga gaa gcc agt ttg cag tct cct ccg agc ctt    3309
Gly Arg Lys Trp Leu Gly Glu Ala Ser Leu Gln Ser Pro Pro Ser Leu
        1015                1020                1025 ctc ctt caa gct aat gaa gag atg ttt cca agg aaa gtt ctg cta cca    3357
Leu Leu Gln Ala Asn Glu Glu Met Phe Pro Arg Lys Val Leu Leu Pro
        1030                1035                1040 agt tct aat cct gta tct cca gaa acg acg caa cat tcc tct aat caa    3405
Ser Ser Asn Pro Val Ser Pro Glu Thr Thr Gln His Ser Ser Asn Gln
    1045                1050                1055 aac cca gct gga tta act acc aag cag tct aat ttg gag aga acg cat    3453
Asn Pro Ala Gly Leu Thr Thr Lys Gln Ser Asn Leu Glu Arg Thr His
1060                1065                1070                1075 tct tac aaa gtg cct gag aaa gtt tct tct ggg act aac att cct aaa    3501
Ser Tyr Lys Val Pro Glu Lys Val Ser Ser Gly Thr Asn Ile Pro Lys
            1080                1085                1090 aaa agt gcc gtg atg ccg tca cca gga aca tct tcc agc ccc tta gaa    3549
Lys Ser Ala Val Met Pro Ser Pro Gly Thr Ser Ser Ser Pro Leu Glu
        1095                1100                1105
```

```
cct gcc atc tca gcc caa gag ctg gac gct cgg act ggg cta tat gcc    3597
Pro Ala Ile Ser Ala Gln Glu Leu Asp Ala Arg Thr Gly Leu Tyr Ala
    1110                1115                1120 agg ttg gtg gaa gca agg cag aaa cac gct aat aag atg gat gta cct    3645
Arg Leu Val Glu Ala Arg Gln Lys His Ala Asn Lys Met Asp Val Pro
    1125                1130                1135 cca gct att tta gca aca aac aag gtt ctg ctg gac atg gct aaa atg    3693
Pro Ala Ile Leu Ala Thr Asn Lys Val Leu Leu Asp Met Ala Lys Met
1140                1145                1150                1155 aga ccg act act gtt gaa aac atg aaa cag atc gac ggt gtc tct gaa    3741
Arg Pro Thr Thr Val Glu Asn Met Lys Gln Ile Asp Gly Val Ser Glu
                1160                1165                1170 ggc aaa gct gct ctg ttg gcc cct ctg ttg gga gtc atc aaa cat ttc    3789
Gly Lys Ala Ala Leu Leu Ala Pro Leu Leu Gly Val Ile Lys His Phe
    1175                1180                1185 tgt caa gta act agt gtt cag aca gac ctc ctt tcc agt gcc aaa cct    3837
Cys Gln Val Thr Ser Val Gln Thr Asp Leu Leu Ser Ser Ala Lys Pro
        1190                1195                1200 cac aag gaa cag gag aaa agt cag gag atg gaa aag aaa gac tgc tca    3885
His Lys Glu Gln Glu Lys Ser Gln Glu Met Glu Lys Lys Asp Cys Ser
    1205                1210                1215 ctc ccc cag tct gtg gcc gtc aca tac act cta ttc cag gaa aag aaa    3933
Leu Pro Gln Ser Val Ala Val Thr Tyr Thr Leu Phe Gln Glu Lys Lys
1220                1225                1230                1235 atg ccc tta cac agc ata gct gag aac agg ctc ctg cct ctc aca gca    3981
Met Pro Leu His Ser Ile Ala Glu Asn Arg Leu Leu Pro Leu Thr Ala
                1240                1245                1250 gtc ggc atg cac tta gcc cag gcg gtg aaa gcc ggc tac ccc ctg gat    4029
Val Gly Met His Leu Ala Gln Ala Val Lys Ala Gly Tyr Pro Leu Asp
    1255                1260                1265 atg gag cga gct ggc ctg acc cca gag act tgg aag att att atg gat    4077
Met Glu Arg Ala Gly Leu Thr Pro Glu Thr Trp Lys Ile Ile Met Asp
    1270                1275                1280 gtc atc cga aac cct ccc atc aac tca gat atg tat aaa gtt aaa ctc    4125
Val Ile Arg Asn Pro Pro Ile Asn Ser Asp Met Tyr Lys Val Lys Leu
    1285                1290                1295 atc aga atg tta gtt cct gaa aac atc gac acg tac ctc atc cac atg    4173
Ile Arg Met Leu Val Pro Glu Asn Ile Asp Thr Tyr Leu Ile His Met
1300                1305                1310                1315 gcg att gag att ctt cag agt ggt tcc gac agc aga acc cag cct cct    4221
Ala Ile Glu Ile Leu Gln Ser Gly Ser Asp Ser Arg Thr Gln Pro Pro
        1320                1325                1330 tgt gat tcc agc agg aag agg cgt ttc ccc agc tct gca gag agt tgt    4269
Cys Asp Ser Ser Arg Lys Arg Arg Phe Pro Ser Ser Ala Glu Ser Cys
        1335                1340                1345 gag agc tgt aag gag agc aaa gag gtg gtc acc gag acc aag gca tca    4317
Glu Ser Cys Lys Glu Ser Lys Glu Val Val Thr Glu Thr Lys Ala Ser
    1350                1355                1360 tct tca gag tca aag aga aaa tta cct gag tgg ttt gcc aaa gga aat    4365
Ser Ser Glu Ser Lys Arg Lys Leu Pro Glu Trp Phe Ala Lys Gly Asn
    1365                1370                1375 gtg ccc tca gct gat acc ggc agc tca tca atg gcc aag acc aaa        4413
Val Pro Ser Ala Asp Thr Gly Ser Ser Ser Met Ala Lys Thr Lys
1380                1385                1390                1395 aag aaa ggt ctc ttt agt t aagatgacaa cgatggaaca gtttgtgtgt         4462
Lys Lys Gly Leu Phe Ser
                1400
cctacatctt cattcctata aagaatgaaa agaaatattt taacgatgac aacgatggaa   4522
cagtttgtgt gtcctacatc ttcattccta taaagaatga aagaaatat tttaacctca    4582
```

-continued

```
aaattattta aagtccaaag tgaagctcac ctaaacgtcg agccatagag tctttaattg    4642
cccgttggca gttgagctac agtatctgaa ccttctgaga cccggagtgc agcatagact    4702
gtgaagtcgg cttcctttcc gattgccttc cgaaccggtg ccactgtcag gttgcagtct    4762
ttctcttctt gcagcagtgt gtgttggaaa tggaggctgt gtcgctttga catatagaac    4822
agatcaatag ttgcataggg acagatatga agatacagcc ggtctttgct ttcttatgca    4882
gatgcctgta tgacagtatc agtgcaccag cccagccagg gagacatcag cttccattta    4942
aaaagggaaa gcggacaagg actccagtta cagaaacaac taaattctat gcattttctg    5002
cagtctttat tatttctcaa tcaaaagtgt tctttgtact gaatagtaaa tatactaaat    5062
tttcattttt taaattgttg tgagtgcctt caatatttga agatgccaat ttttaatgtc    5122
ttatgtttca caaagaatta aaaaactgaa aattcaactc tgttcttggt aaactattgt    5182
tatataaatt taagcagttt accatatagc taaatatatt caaagccttg gattaacttt    5242
tttttgtaaa tagaaatgga ctgttattaa tgtaggaaaa aatacacctg aattcagaga    5302
agttaaaaaa aagtcactca gggttccatt aggaaagaat caaagccatt tttttttca    5362
atcagccaga ctccctcgta ttcattttct taatttgaat cttattataa gacattcaaa    5422
ctataattaa aacatagaaa ctcccacatt ctcattttc tgctattacc agaaggtagc    5482
tttccgtata tcacgcataa tctccagttg cttctatttc tctgtgcctt aaactgtgtc    5542
tataatgcat gaggtggtat tctctgtggc agtgtcagcg ctcgggtccc tgctggttgc    5602
ggtggcctgc tgcaggaaaa cgtctgcttc attgttttga cttatgagtt gaactgggtt    5662
ttctttcctt cgtggaattg aaaaacaaag cttgggggca aaagtatgc ttggtttttt    5722
agacttgtta tttggcagac attttctcaa gattcaatga agttagcctg ttgctttaag    5782
gaaaatgact taccaatatt attgccagta ataaaattga gatttctagc aaaaattaca    5842
attctggtga acaggtgtcc ttcactggga gcctgggcag ctttccttga cctgagggct    5902
tttctaatga gatgaataaa ataaacacat tatttttgat actatctaaa gtttcatctg    5962
tatctggaac atctaagtga cccaagaaat cagtgtttaa tggacaacta agacacgtta    6022
taatatagca tatatagtaa tgtagtcaag gaagagccca tggccgtccc ttcagataca    6082
cactgaaaat aatcacgaag caacagctac agttttcatt tcaaagattt aaagtttcaa    6142
agattctcta ccattatttg aaaagtattt tcaaatagct tttcctaata tagcacacac    6202
acacacacac acacacacac acacagactg aatacagtag accagactcc aggctcttct    6262
tctcctgaac tcatccacac aacgagaaca tttacagaaa tgaaatgggg ccatccttgt    6322
cttttttta aatgtaaatg tgattttaaa acgaacaata tttgtgctaa attgtaattg    6382
gtttactgca gccatttta aatgaatcaa taaatctttg aaaaagcct ccaaaaaaaa    6442
aaaaaaaaa aaaaaaaaa aaaaaaaaa aaaa                                   6476
```

<210> SEQ ID NO 6
<211> LENGTH: 1401
<212> TYPE: PRT
<213> ORGANISM: Murine

<400> SEQUENCE: 6

```
Met Glu Thr Thr Ser Leu Gln Arg Lys Phe Pro Glu Trp Met Ser Met
  1               5                  10                  15

Gln Ser Gln Arg Cys Ala Thr Glu Glu Lys Ala Cys Val Gln Lys Ser
             20                  25                  30
```

-continued

```
Val Leu Glu Asp Asn Leu Pro Phe Leu Glu Phe Pro Gly Ser Ile Val
        35                  40                  45

Tyr Ser Tyr Glu Ala Ser Asp Cys Ser Phe Leu Ser Glu Asp Ile Ser
    50                  55                  60

Met Arg Leu Ser Asp Gly Asp Val Val Gly Phe Asp Met Glu Trp Pro
65                  70                  75                  80

Pro Ile Tyr Lys Pro Gly Lys Arg Ser Arg Val Ala Val Ile Gln Leu
            85                  90                  95

Cys Val Ser Glu Asn Lys Cys Tyr Leu Phe His Ile Ser Ser Met Ser
                100                 105                 110

Val Phe Pro Gln Gly Leu Lys Met Leu Leu Glu Asn Lys Ser Ile Lys
            115                 120                 125

Lys Ala Gly Val Gly Ile Glu Gly Asp Gln Trp Lys Leu Leu Arg Asp
    130                 135                 140

Phe Asp Val Lys Leu Glu Ser Phe Val Glu Leu Thr Asp Val Ala Asn
145                 150                 155                 160

Glu Lys Leu Lys Cys Ala Glu Thr Trp Ser Leu Asn Gly Leu Val Lys
                165                 170                 175

His Val Leu Gly Lys Gln Leu Leu Lys Asp Lys Ser Ile Arg Cys Ser
            180                 185                 190

Asn Trp Ser Asn Phe Pro Leu Thr Glu Asp Gln Lys Leu Tyr Ala Ala
    195                 200                 205

Thr Asp Ala Tyr Ala Gly Leu Ile Ile Tyr Gln Lys Leu Gly Asn Leu
210                 215                 220

Gly Asp Thr Val Gln Val Phe Ala Leu Asn Lys Ala Glu Glu Asn Leu
225                 230                 235                 240

Pro Leu Glu Met Lys Lys Gln Leu Asn Leu Ile Ser Glu Glu Met Arg
                245                 250                 255

Asp Leu Ala Asn Arg Phe Pro Val Thr Cys Arg Asn Leu Glu Thr Leu
            260                 265                 270

Gln Arg Val Pro Val Ile Leu Lys Ser Ile Ser Glu Asn Leu Cys Ser
    275                 280                 285

Leu Arg Lys Val Ile Cys Gly Pro Thr Asn Thr Glu Thr Arg Leu Lys
290                 295                 300

Pro Gly Ser Ser Phe Asn Leu Leu Ser Ser Glu Asp Ser Ala Ala Ala
305                 310                 315                 320

Gly Glu Lys Glu Lys Gln Ile Gly Lys His Ser Thr Phe Ala Lys Ile
                325                 330                 335

Lys Glu Glu Pro Trp Asp Pro Gly Leu Asp Ser Leu Val Lys Gln Glu
            340                 345                 350

Glu Val Asp Val Phe Arg Asn Gln Val Lys Gln Glu Lys Gly Glu Ser
    355                 360                 365

Glu Asn Glu Ile Glu Asp Asn Leu Leu Arg Glu Asp Met Glu Arg Thr
370                 375                 380

Cys Val Ile Pro Ser Ile Ser Glu Asn Glu Leu Gln Asp Leu Glu Gln
385                 390                 395                 400

Gln Ala Lys Glu Glu Lys Tyr Asn Asp Val Ser His Gln Leu Ser Glu
                405                 410                 415

His Leu Ser Pro Asn Asp Asp Glu Asn Asp Ser Ser Tyr Ile Ile Glu
            420                 425                 430

Ser Asp Glu Asp Leu Glu Met Glu Met Leu Lys Ser Leu Glu Asn Leu
435                 440                 445
```

-continued

```
Asn Ser Asp Met Val Glu Pro Thr His Ser Lys Trp Leu Glu Met Gly
450                     455                     460

Thr Asn Gly Cys Leu Pro Pro Glu Glu Glu Asp Gly His Gly Asn Glu
465                     470                     475                 480

Ala Ile Lys Glu Glu Gln Glu Glu Asp His Leu Leu Pro Glu Pro
                        485                     490                 495

Asn Ala Lys Gln Ile Asn Cys Leu Lys Thr Tyr Phe Gly His Ser Ser
                500                     505                     510

Phe Lys Pro Val Gln Trp Lys Val Ile His Ser Val Leu Glu Glu Arg
            515                     520                     525

Arg Asp Asn Val Val Val Met Ala Thr Gly Tyr Gly Lys Ser Leu Cys
        530                     535                     540

Phe Gln Tyr Pro Pro Val Tyr Thr Gly Lys Ile Gly Ile Val Ile Ser
545                     550                     555                     560

Pro Leu Ile Ser Leu Met Glu Asp Gln Val Leu Gln Leu Glu Leu Ser
                565                     570                     575

Asn Val Pro Ala Cys Leu Leu Gly Ser Ala Gln Ser Lys Asn Ile Leu
                580                     585                     590

Gly Asp Val Lys Leu Gly Lys Tyr Arg Val Ile Tyr Ile Thr Pro Glu
            595                     600                     605

Phe Cys Ser Gly Asn Leu Asp Leu Leu Gln Lys Leu Asp Ser Ser Ile
610                     615                     620

Gly Ile Thr Leu Ile Ala Val Asp Glu Ala His Cys Ile Ser Glu Trp
625                     630                     635                     640

Gly His Asp Phe Arg Ser Ser Phe Arg Met Leu Gly Ser Leu Lys Thr
                645                     650                     655

Ala Leu Pro Leu Val Pro Val Ile Ala Leu Ser Ala Thr Ala Ser Ser
                660                     665                     670

Ser Ile Arg Glu Asp Ile Ile Ser Cys Leu Asn Leu Lys Asp Pro Gln
            675                     680                     685

Ile Thr Cys Thr Gly Phe Asp Arg Pro Asn Leu Tyr Leu Glu Val Gly
            690                     695                     700

Arg Lys Thr Gly Asn Ile Leu Gln Asp Leu Lys Pro Phe Leu Val Arg
705                     710                     715                     720

Lys Ala Ser Ser Ala Trp Glu Phe Glu Gly Pro Thr Ile Ile Tyr Cys
                725                     730                     735

Pro Ser Arg Lys Met Thr Glu Gln Val Thr Ala Glu Leu Gly Lys Leu
                740                     745                     750

Asn Leu Ala Cys Arg Thr Tyr His Ala Gly Met Lys Ile Ser Glu Arg
            755                     760                     765

Lys Asp Val His His Arg Phe Leu Arg Asp Glu Ile Gln Cys Val Val
        770                     775                     780

Ala Thr Val Ala Phe Gly Met Gly Ile Asn Lys Ala Asp Ile Arg Lys
785                     790                     795                     800

Val Ile His Tyr Gly Ala Pro Lys Glu Met Glu Ser Tyr Tyr Gln Glu
                805                     810                     815

Ile Gly Arg Ala Gly Arg Asp Gly Leu Gln Ser Ser Cys His Leu Leu
            820                     825                     830

Trp Ala Pro Ala Asp Phe Asn Thr Ser Arg Asn Leu Leu Ile Glu Ile
            835                     840                     845

His Asp Glu Lys Phe Arg Leu Tyr Lys Leu Lys Met Met Val Lys Met
850                     855                     860
```

-continued

```
Glu Lys Tyr Leu His Ser Ser Gln Cys Arg Arg Ile Ile Leu Ser
865                 870                 875                 880

His Phe Glu Asp Lys Cys Leu Gln Lys Ala Ser Leu Asp Ile Met Gly
                885                 890                 895

Thr Glu Lys Cys Cys Asp Asn Cys Arg Pro Arg Leu Asn His Cys Leu
            900                 905                 910

Thr Ala Asn Asn Ser Glu Asp Ala Ser Gln Asp Phe Gly Pro Gln Ala
            915                 920                 925

Phe Gln Leu Leu Ser Ala Val Asp Ile Leu Gln Glu Lys Phe Gly Ile
    930                 935                 940

Gly Ile Pro Ile Leu Phe Leu Arg Gly Ser Asn Ser Gln Arg Leu Pro
945                 950                 955                 960

Asp Lys Tyr Arg Gly His Arg Leu Phe Gly Ala Gly Lys Glu Gln Ala
                965                 970                 975

Glu Ser Trp Trp Lys Thr Leu Ser His His Leu Ile Ala Glu Gly Phe
            980                 985                 990

Leu Val Glu Val Pro Lys Glu Asn Lys Tyr Ile Lys Thr Cys Ser Leu
        995                 1000                1005

Thr Lys Lys Gly Arg Lys Trp Leu Gly Glu Ala Ser Leu Gln Ser Pro
    1010                1015                1020

Pro Ser Leu Leu Gln Ala Asn Glu Glu Met Phe Pro Arg Lys Val
1025                1030                1035                1040

Leu Leu Pro Ser Ser Asn Pro Val Ser Pro Glu Thr Thr Gln His Ser
            1045                1050                1055

Ser Asn Gln Asn Pro Ala Gly Leu Thr Thr Lys Gln Ser Asn Leu Glu
            1060                1065                1070

Arg Thr His Ser Tyr Lys Val Pro Glu Lys Val Ser Ser Gly Thr Asn
            1075                1080                1085

Ile Pro Lys Lys Ser Ala Val Met Pro Ser Pro Gly Thr Ser Ser Ser
            1090                1095                1100

Pro Leu Glu Pro Ala Ile Ser Ala Gln Glu Leu Asp Ala Arg Thr Gly
1105                1110                1115                1120

Leu Tyr Ala Arg Leu Val Glu Ala Arg Gln Lys His Ala Asn Lys Met
            1125                1130                1135

Asp Val Pro Pro Ala Ile Leu Ala Thr Asn Lys Val Leu Leu Asp Met
            1140                1145                1150

Ala Lys Met Arg Pro Thr Thr Val Glu Asn Met Lys Gln Ile Asp Gly
            1155                1160                1165

Val Ser Glu Gly Lys Ala Ala Leu Leu Ala Pro Leu Leu Gly Val Ile
    1170                1175                1180

Lys His Phe Cys Gln Val Thr Ser Val Gln Thr Asp Leu Leu Ser Ser
1185                1190                1195                1200

Ala Lys Pro His Lys Glu Gln Glu Lys Ser Gln Glu Met Glu Lys Lys
            1205                1210                1215

Asp Cys Ser Leu Pro Gln Ser Val Ala Val Thr Tyr Thr Leu Phe Gln
            1220                1225                1230

Glu Lys Lys Met Pro Leu His Ser Ile Ala Glu Asn Arg Leu Leu Pro
            1235                1240                1245

Leu Thr Ala Val Gly Met His Leu Ala Gln Ala Val Lys Ala Gly Tyr
    1250                1255                1260

Pro Leu Asp Met Glu Arg Ala Gly Leu Thr Pro Glu Thr Trp Lys Ile
1265                1270                1275                1280
```

-continued

```
Ile Met Asp Val Ile Arg Asn Pro Pro Ile Asn Ser Asp Met Tyr Lys
            1285                1290                1295

Val Lys Leu Ile Arg Met Leu Val Pro Glu Asn Ile Asp Thr Tyr Leu
            1300                1305                1310

Ile His Met Ala Ile Glu Ile Leu Gln Ser Gly Ser Asp Ser Arg Thr
            1315                1320                1325

Gln Pro Pro Cys Asp Ser Ser Arg Lys Arg Arg Phe Pro Ser Ser Ala
    1330                1335                1340

Glu Ser Cys Glu Ser Cys Lys Glu Ser Lys Glu Val Val Thr Glu Thr
1345                1350                1355                1360

Lys Ala Ser Ser Ser Glu Ser Lys Arg Lys Leu Pro Glu Trp Phe Ala
            1365                1370                1375

Lys Gly Asn Val Pro Ser Ala Asp Thr Gly Ser Ser Ser Ser Met Ala
            1380                1385                1390

Lys Thr Lys Lys Lys Gly Leu Phe Ser
        1395                1400
```

ASSAYS FOR COMPOUNDS WHICH EXTEND LIFE SPAN

RELATED APPLICATIONS

This application claims the benefit of U.S. Provisional Application Serial No. 60/054,629, filed Aug. 4, 1997, the entire teachings of which are incorporated herein by reference.

GOVERNMENT FUNDING

Work described herein was funded by Grant No. RO0 AG11119-05 from the National Institutes of Health. The U.S. Government has certain rights in the invention.

BACKGROUND OF THE INVENTION

One of the great challenges of modern biology is an explanation of aging at the organismal level. The fundamental property of aging is manifest in organisms as complex as humans and as simple as the single-celled yeast, *Saccharomyces cerevisiae*. The ability to extend life span and forestall senescence has long been the subject of debate and exploration.

Recent studies of the premature aging disease, Werner's syndrome, provide possible clues about the aging process. Beginning soon after puberty, Werner's syndrome patients display many symptoms of old age, including graying and loss of hair, osteoporosis, cataracts, atherosclerosis, loss of skin elasticity and a propensity for certain cancers. Because cells isolated from Werner's patients divide approximately half as many times in culture as those from normal individuals (Salk et al., *Cytogenet. Cell. Genet.* 30:108 (1981); G. M. Martin, *Adv. Exp. Med. Biol.* 190:161 (1985)), it is possible that both organismal aging and cellular aging are manifestations of the same process (Lombard and Guarente, *Trends Genet.* 12:283 (1996)).

SUMMARY OF THE INVENTION

The premature aging disease, Werner's syndrome, results from mutations in a single recessive gene, WRN. As described herein, mutation of the yeast WRN homolog, SGS1, causes premature aging in yeast mother cells. The aging-induced phenotype of sterility and redistribution of the Sir3 silencing protein from telomeres to the nucleolus occurs prematurely in sgs1 yeast cells. Further, the nucleolus is enlarged and fragmented in these cells, a change that also occurs in old wild type cells. These findings suggest a remarkably conserved mechanism of cellular aging which may be related to nucleolar structure. The observation that mutation of the yeast Werner's homolog, SGS1, results in premature aging suggests that a common mechanism underlies aging in eukaryotes as diverse as yeast and humans. Thus, insight into the aging process in model systems can provide insight into aging in humans.

The subject invention pertains to methods of identifying agents or compounds which inhibit the replication and/or accumulation of DNA circles, e.g., ribosomal DNA (rDNA) circles, comprising an autonomously replicating sequence (ARS), e.g., rDNA ARS, in cells. The invention also encompasses methods of assessing the ability of a compound to extend life span of a cell, comprising contacting a cell or cells (referred to as a test cell or cells) with a compound which inhibits the replication and/or accumulation of DNA circles comprising an ARS in cells, and assessing the life span of the test cell relative to a comparable cell or cells which was not contacted with the compound (a control cell or cells). If the life span of the test cell is longer than the life span of the control cell, then the compound extends life span. The invention also relates to methods of extending life span, comprising administering to a cell a compound which inhibits replication and/or accumulation of rDNA circles in the cell, with the result that the life span of the cell is extended (is longer than it would have been in the absence of the compound). These compounds can be compounds identified by the methods described herein, derivatives (modified forms) of compounds identified by the present methods, or compounds identified by another method (e.g., computer modeling of compounds designed with reference to structures and/or characteristics of compounds identified by the present method) and synthesized by known methods (e.g., chemical synthesis, peptide chemistry).

As described herein, a mouse gene referred to as mWRN, which is a homolog of Sgs1p and WRN, has been discovered. This invention also pertains to isolated mWRN, or an active derivative or fragment thereof; in a particular embodiment, the isolated mWRN protein has the amino acid sequence of SEQ ID NO: 6 (FIG. 5). In one embodiment, the polypeptide is a fragment having mWRN activity, e.g., binding or enzymatic activity. In another embodiment, the polypeptide is a derivative possessing substantial sequence identity with endogenous mWRN. In particular embodiments, the mWRN protein is purified to homogeneity or is substantially free of other proteins.

The invention also pertains to an isolated nucleic acid molecule which encodes mWRN, or an active derivative or fragment thereof. In a particular embodiment, the nucleic acid molecule has the nucleotide sequence of SEQ ID NO: 5 (FIG. 4). In one embodiment, the nucleic acid molecule encodes a polypeptide fragment having mWRN activity. In another embodiment, the nucleic acid molecule encodes a derivative of mWRN possessing substantial sequence identity with endogenous mWRN. In particular embodiments, the isolated nucleic acid molecule encodes mWRN with the same amino acid sequence as endogenous mWRN. In another embodiment, the isolated nucleic acid molecule has the same nucleotide sequence as the endogenous gene encoding mWRN.

The invention also relates to DNA constructs comprising the nucleic acid molecules described above operatively linked to a regulatory sequence, and to recombinant host cells, such as bacterial cells, fungal cells, plant cells, insect cells and mammalian cells, comprising the nucleic acid molecules described above operatively linked to a regulatory sequence. The invention also pertains to an antibody, or an antigen-binding fragment thereof, which selectively binds to mWRN, or an active derivative or fragment thereof; in a particular embodiment, the antibody is a monoclonal antibody.

The invention also pertains to a mouse and its progeny having a suppressed level of expression of the mWRN gene. The invention further relates to a mouse and its progeny in which the mWRN gene is suppressed, either physically or functionally. The invention also relates to embryonic stem cell lines containing a mWRN knockout construct.

In another embodiment, the invention relates to a method of screening a compound for the ability to alter life span comprising administering the compound to a mouse with a suppressed level of mWRN expression and assaying the mouse for altered life span. The invention also relates to compounds identified by assays described herein.

BRIEF DESCRIPTION OF THE DRAWINGS

FIG. 1A shows the results for wild type and sgs1::HIS3. FIG. 1B shows the results for wild type, ada1::hisG, and hap5::hisG. Average life spans were as follows (sample sizes are given in parentheses): wild type, 24.5 divisions (39); sgs1, 9.5 divisions (30); ada1, 3.3 divisions (23); and hap5, 16.6 divisions (28).

FIG. 2A shows results for sgs1 cells; FIG. 2B shows results for sgs1 hm1αΔ cells. FIG. 2C shows the results for hap5 cells, and FIG. 2D shows results for ada1 cells.

FIG. 3A illustrates restriction maps of two overlapping genomic clones containing a portion of the helicase domain. The fragment used as a hybridization probe to screen neomycin-resistant colonies is bracketed in the longer genomic clone. FIG. 3B illustrates the mWRN targeting construct. The direction of transcription of both the mWRN gene and the Ogeo cassette is indicated. In both FIGS. 3A and 3B, not all HindIII sites are indicated.

Figure 4E:
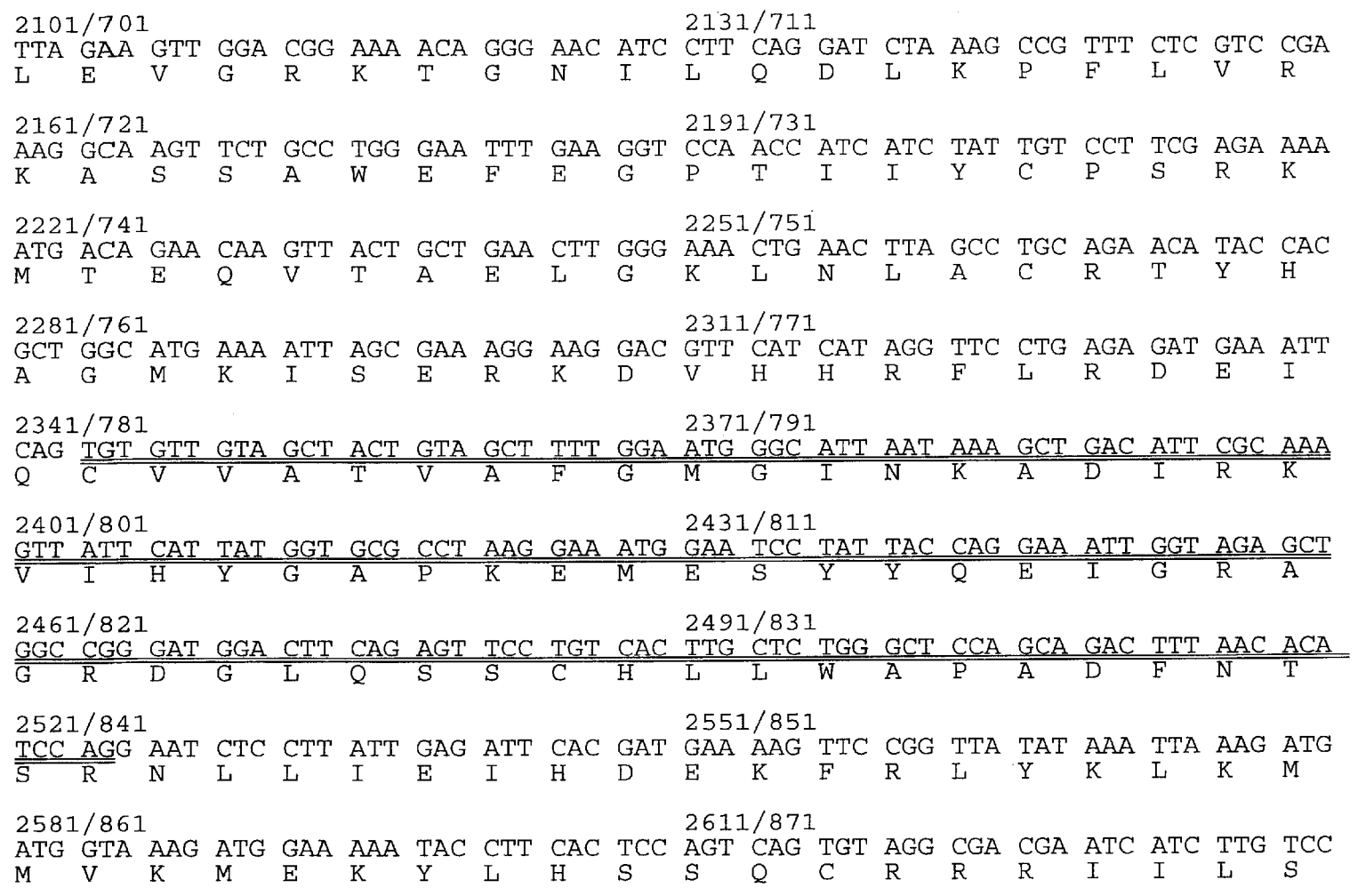

FIGS. 4A–4I illustrate the nucleic acid sequence (SEQ ID NO: 5) and the amino acid sequence (SEQ ID NO: 6) of the mWRN gene. Stops in the 5' untranslated region are underlined and potential polyadenylation sites in the 3' untranslated region are in bold. Double underlining indicates the exon deleted in the targeting construct.

DETAILED DESCRIPTION OF THE INVENTION

Figure 1A:
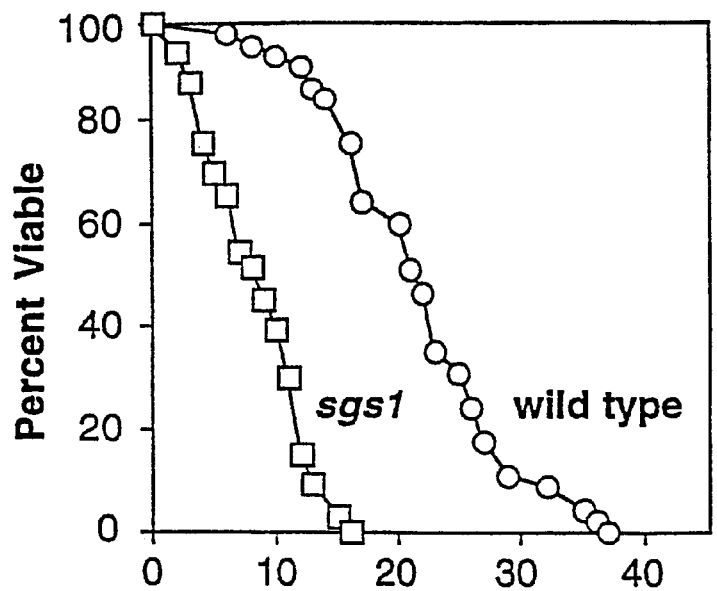
FIGS. 1A and 1B illustrate that mutant sgs1 cells have a short life span. Mortality curves of wild type (W303-1A MATa ade2-1 can1-100 his3-11,15 leu2-3,112 trp1-1 ura3-1, from R. Rothstein) and isogenic mutant derivatives, sgs1::HIS3, ada1::hisG, and hap5::hisG were determined.

Werner's syndrome results from a recessive mutation in a single gene, WRN, which encodes a protein with substantial similarity to the E. coli RecQ DNA helicase (Yu et al., Science 272:258 (1996)). Other members of the RecQ helicase family include human BLM (mutations in which cause Bloom's syndrome; Ellis et al., Cell 83:655 (1995)), human RECQL (Puranam and Blackshear, J. Biol. Chem. 269:29838 (1994); Seki et al., Nucl. Acids Res. 22:4566 (1994)), and SGS1 of Saccharomyces cerevisiae (Gangloff et al., Mol. Cell. Biol. 14:8391 (1994); Watt et al., Cell 81:253 (1995)). Bloom's syndrome is characterized by a high rate of cancers and sunlight sensitivity, but not typical aging phenotypes (German, Medicine 72:393 (1993)). The different symptoms of Werner's and Bloom's syndromes suggest that WRN has a functional specificity that underlies premature aging.

The yeast WRN homolog is known as SGS1. Mutations in SGS1 were first identified as suppressors of the slow growth phenotype of cells lacking topoisomerase III (TOP3) activity (Gangloff et al., Mol. Cell. Biol. 14:8391 (1994)). SGS1 has since been shown to suppress recombination at the ribosomal DNA (rDNA) array (Christman et al., Cell 55:413 (1988)) and other loci (Watt et al., Genetics 144:935 (1996)), as well as maintaining the fidelity of chromosome segregation during cell division (Watt et al., Cell 81:253 (1995)). Sgs1p interacts genetically and physically with both topoisomerases II and III (Gangloff et al., Mol. Cell. Biol. 14:8391 (1994); Watt et al., Cell 81:253 (1995)), suggesting that the DNA helicase and topoisomerase activities are coupled. Based on complementation assays, Sgs1p function requires the C-terminus, but surprisingly, not DNA helicase activity (Lu et al., Nature 383:678 (1996)).

Cell division in S. cerevisiae is asymmetric, giving rise to a large mother and a small daughter cell (Hartwell and Unger, J. Cell Biol. 75:4222 (1977); Kennedy et al., J. Cell Biol. 127:1985 (1994)). Yeast aging is defined by the relatively fixed number of cell divisions undergone by mother cells (Muller et al., Aging Dev. 12:47 (1980)), as well as characteristic changes during their life span (Jazwinski, Science 273:54 (1996)), such as cell enlargement (Mortimer and Johnson, Nature 183:1751 (1959)) and sterility (Muller, J. Microbiol. Serol. 51:1 (1985)). This sterility is due to a loss of transcriptional silencing at HMRa and HMLα loci, and the resulting expression of both a and α mating-type information (Smeal et al., Cell 84:633 (1996)). Loss of telomeric silencing in old yeast cells has also been observed (Kim et al., Biochim. Biophys. Res. Commun. 219:370 (1996)). In young cells, silencing at HM loci and telomeres (Klar et al., Nature 289:239 (1981); Ivy et al., Mol. Cell. Biol. 6:688 (1986); Rine and Herskowitz, Genetics 116:9 (1987)) is mediated by the Sir2/3/4 protein complex (Gottschling et al., Cell 63:751 (1990); Aparicio et al., Cell 66:1279 (1991)). Sir2p silences marker genes inserted at rDNA (Bryk et al., Genes Dev. 11:255 (1997); Smith and Boeke, Genes Dev. 11:241 (1997)) and suppresses recombination between rDNA repeats (Gottleib and Esposito, Cell 56:771 (1989)). The rDNA in yeast consists of a tandem array of about 140 copies of a 9 kb repeat encoding 35S RNA and 5S RNA residing on chromosome 12. This rDNA array is assembled into a crescent-shaped, subnuclear structure termed the nucleolus, in which assembly of ribosomes occurs. The role of Sir3p and Sir4p at the rDNA locus is less clear.

The genes encoding the SIR complex (SIR2, SIR3, and SIR4), as well as UTH4, are determinants of life span in yeast (Kennedy et al., Cell 89:381 (1997)). Null mutations in these genes shorten life span (Kennedy et al., Cell 80:485 (1995)), while over-expression of UTH4 extends life span. It has recently been shown by indirect immunofluorescence that the life span extension by the Sir complex is associated with a redistribution of these factors from telomeres (and HM loci) to the nucleolus in old cells. This redistribution required UTH4 and its yeast homolog YGL023 (Kennedy et al., Cell 89:381 (1997)).

As shown herein, deletion of the yeast homolog of human WRN, a gene responsible for the premature aging disease Werner's syndrome, also causes premature aging in yeast. The conclusion that yeast sgs1 mutants age prematurely is based on three types of data. First, the life span of mother cells is reduced by about 60% compared to wild type. Second, sgs1 mutant cells prematurely assume the aging-specific phenotype of sterility. In contrast, mutations in other yeast genes either did not shorten life span, or did not result in the aging-specific phenotype of sterility. Third, the Sir protein silencing complex redistributes from telomeres to the nucleolus in old sgs1 cells, as observed in old wild type cells.

It is remarkable that mutation of SGS1 and homologs thereof in such diverse organisms as yeast and humans creates a phenocopy of premature aging. This finding suggests that a cellular-based aging mechanism is highly conserved among eukaryotic organisms. The analysis of Sgs1p described herein provides a molecular insight into aging. By immuno-localization, it was found that Sgs1p is concentrated in the nucleolus in yeast cells. By staining old sgs1 cells for Nop1p, enlargement and fragmentation of the nucleolus was noted. These changes further validate the conclusion that sgs1 mutants age prematurely, because identical morphological changes were also observed in very old wild type cells. Interestingly, the nucleolar fragments were often arrayed in an orderly series of spots around the periphery of the nucleolus. It is possible that this configuration represents membrane attachment of the fragments and promotes their biased segregation into mother cells.

It is unlikely that nucleolar enlargement and fragmentation are simply markers of aging which occur, for example, in response to other cellular damage, for at least two reasons. First, an independent study of the relationship between the Sir silencing complex and aging indicated a central role for the nucleolus in determining life span. Second, the concentration of Sgs1p in the nucleolus suggests that a nucleolar defect resulting from the absence of this DNA helicase may be a direct cause of the premature aging of these mutants.

It is also unlikely that nucleolar enlargement and fragmentation represent counteractive measures employed in response to other cellular damage. Since sir3 mutants display nucleolar enlargement and fragmentation earlier than wild type, and also age prematurely, it does not appear that these changes are part of a longevity response. Rather, it appears that nucleolar changes represent a cause of aging, and that this process is repressed by the redistribution of Sir proteins to the nucleolus.

Enlargement and fragmentation of yeast nucleoli have also been observed under certain conditions, including high levels of the nucleolar protein Nop2p (de Beus et al., *J. Cell Biol.* 127:1799 (1994)); inhibition of mRNA export (Kadowaki et al., *Mol. Biol. Cell* 5:1253 (1994); Tani et al., *Mol. Cell. Biol.* 6:1515 (1995)); and a subthreshold level of RNA polymerase I (Oakes et al., *Mol. Cell. Biol.* 13:2441 (1993)). It will be interesting to determine if the fragmented nucleoli in these cases also lead to a short life span and premature sterility, thus strengthening the link between loss of silencing, nucleolar fragmentation, and aging.

Work described herein shows that the age-related enlargement and fragmentation of the nucleolus are due to changes at the rDNA locus that occur with age. One possibility is that aging, in part, results from the inherent instability of the 100 to 200 tandem copies of the 9.1 kb rDNA unit arrayed on chromosome 12 (Warner, *Micro. Rev.* 53:256 (1989)). Homologous recombination between adjacent repeats leads to the excision of unit-sized rDNA circles (Kim and Wang, *Cell* 57:975 (1987)) that replicate via the autonomously replicating sequence (ARS) present in rDNA (Miller and Kowalski, *Mol. Cell. Biol.* 13:5360 (1993)). A segregation bias in such rDNA circles would result in exponential accumulation in old mother cells and cause senescence by titrating important DNA-replication factors. Consistent with this model, cells containing plasmid-borne rDNA molecules have Nop1p staining patterns identical to those described herein in old yeast cells (Nierras et al., Chromosoma, in press (1997); Palladino et al., *Cell* 75:543 (1993)). "Runaway" amplification of extrachromosomal circular DNA is a mechanism of senescence in certain other cases: yeast nibi mutants (Holm, *Cell* 29:585 (1982); Sweeney and Zakian, *Genetics* 122:749 (1989)) and the filamentous fungus, *Podospora anserina* (Jamet-Vierny et al., *Cell* 21:189 (1980)).

As shown herein, unit-sized rDNA circles accumulate exponentially in old yeast mother cells; these rDNA circles are responsible for age-related enlargement and fragmentation of the nucleolus, and appear to nucleate the fragmented nucleolus. In sgs1 mutants, this process is accelerated, resulting in premature aging and shortened life span. Thus, agents or compounds which inhibit (e.g., reduce or prevent) this process are useful to confer extended life span upon cells treated therewith. One embodiment of the subject invention is an assay, e.g., a colony screen, for agents which inhibit the replication and/or accumulation of DNA circles, e.g., rDNA circles, comprising an ARS, such as an rDNA ARS, in cells.

In one embodiment of the assay, yeast cells which are deficient in a gene which is necessary for growth are transformed with a plasmid containing the corresponding gene (a marker gene) and an ARS. Suitable marker genes include, but are not limited to, ADE2, LEU2, URA3, HIS3, TRP1, lacZ, GFP and LYS2. Transformants are able to grow in media deficient in the nutrient encoded by the marker gene; non-transformed cells will not. For example, ade2- yeast cells transformed with a plasmid comprising the ADE2 gene are able to grow in the absence of adenine. The absence of the ADE2 gene product results in a block in the adenine biosynthetic pathway, which leads to the accumulation of a red pigment (normally yeast colonies are white). In transformants, the plasmid is either stably integrated into the genome or present as an unstable DNA circle in the cell. The two classes of transformants are distinguishable because of the segregation bias of the plasmid DNA circles containing the ARS and marker gene. These circles preferentially remain with the mother cell, and, thus, offspring are unable to grow in the absence of the necessary nutrient (e.g., adenine). As a result, colonies in which the plasmid has stably integrated (class I transformants) will grow exponentially, and colonies which contain the plasmid as an unstable DNA circle (class II transformants) will not grow exponentially but rather linearly. The difference between the two classes of transformants will be apparent by colony size in three to four days.

The two classes of transformants can then be used in an assay to assess the ability of compounds to inhibit the replication and/or accumulation of the plasmid DNA circles. Both the class I and class II transformants are grown in the absence of the necessary nutrient encoded by the marker gene. The cells of each class are transferred to separate, duplicate microtiter dishes (also deficient in the necessary nutrient) which contain a compound to be assessed in each well at an appropriate concentration or amount. Growth in each well is assessed, and compounds which inhibit growth are identified. Compounds which inhibit the growth of both class I and class II transformants are likely to be non-specific inhibitors and are generally not useful for further study. However, compounds which inhibit the growth of class II transformants but do not affect class I transformants are likely to be specific inhibitors of the replication and/or accumulation of DNA circles. Such compounds are useful to inhibit the age-related enlargement and fragmentation of the nucleolus and corresponding aging; thus, these compounds can be used to extend the life span of cells treated therewith.

A similar screening strategy can be adapted for use in mammalian cells. For example, a plasmid comprising a marker gene and an ARS is inserted into the germline cells of a mammal, e.g., a mouse. Any suitable marker gene which allows one to differentiate between cells which contain the plasmid and cells which do not, including, but not limited to, LACZ and GFP, can be used. Preferably, the marker gene produces a phenotypic effect when expressed. In an assay utilizing mammalian cells, stem cells are equivalent to yeast mother cells, and differentiated cells are equivalent to yeast daughter cells, of the yeast-based assay described above. The mammal is treated with an agent to be tested, and the effect of the agent on the accumulation and/or replication of the plasmid in stem cells and differentiated cells is assessed. In one embodiment, the presence and/or amount of the plasmid in stem cells can be assessed by analyzing an organ or portion thereof which has a high concentration of stem cells; for example, the presence and/or amount of the plasmid can be assessed in crypt cells. Agents which inhibit the replication and/or accumulation of the plasmid are useful to extend the life span of the mammal.

The ability of compounds identified by the assays described above to confer extended life span can also be assessed by assaying the life span of cells, e.g., yeast cells or mammalian cells, treated with the identified compound. For example, methods for isolating yeast cells with an increased life span are described in U.S. Pat. No. 5,919,618, issued Jul. 6, 1999; the teachings of this application are incorporated herein by reference. These assays, as well as others known in the art, are suitable for use in determining whether cells treated with an identified compound exhibit extended life span relative to untreated cells.

For example, techniques described herein can be used to isolate cells with increased life span from yeast and other cell types (e.g., mammalian cells). Any cell strain for which the normal life span is known can be utilized. The life span of the strain can be determined by calculating the mean number of generations before senescence in a sample of colonies of the strain of interest. The average life span of normal (wild type) cells is used as a comparison standard (control) against which the life span of test cells, e.g., cells of the same strain which are treated with an agent of interest, can be measured. Test cells are treated with a compound of interest, the life span of the treated test cells is determined, and the life span of the treated test cells is compared with the average life span of normal cells of the same strain. For example, cells with increased life spans can be isolated as follows:

Stress-Resistance Method

Yeast cells that have been treated with a compound of interest are plated with minimal nutrients (including carbon and nitrogen sources, as well as the amino acids and nucleotides that are required by the particular strain for growth). The minimal plates are replica-plated to plates lacking vital nutrients, such as nitrogen and carbon (the starvation plates). After incubation of the starvation plates at a temperature appropriate for growth, for several days, the starvation plates are replicated back to rich media plates. The rare colonies containing living cells when plated back onto rich medium (the "starvation resistant" colonies) are then examined to determine whether the life span is extended. Life span is calculated as described above.

Cell Surface Labeling Method

This method takes advantage of the fact that the cell surface (including the cell membrane and cell wall) of a daughter cell in some budding yeast, such as *S. cerevisiae*, is fabricated entirely of new materials: when the cell surface of the mother cell is labeled, the surface of the daughter cells remains unlabeled. In one embodiment, the cell surface is labeled with biotin. When avidin linked to fluorescence is coupled to the biotin, the cell surface fluoresces. Alternatively, any other method of labelling the cell surface with a fluorescent marker is appropriate. Daughter cells remain unlabeled (will not fluoresce). Fluorescently-labeled yeast cells are plated and cultured for a period of time greater than the life span of the control cells which have not been treated with a compound of interest (as measured by time necessary for one cell division, multiplied by the number of divisions, or generations, in the life span). If desired, the yeast cells may be sampled at regular time intervals in order to monitor the plating efficiency of the cells; the efficiency will drop precipitously after the chronological life span has passed. The yeast cells are then subjected to fluorescence-activated cell sorting (FACS), to isolate the fluorescently labeled cells. The fluorescent cells are then replated; only cells with increased life spans will grow.

Temperature-Sensitive Method

A temperature-sensitive strain of yeast, in which the offspring die at the non-permissive temperature, is utilized in this method. For example, yeast cells with a mutation in the mdm2-2 gene (also known as the ole-1 gene) (McConnell, et al., *J. Cell Biol.* 111:967–976 (1990)) bud forth living daughter cells at 30° C., but not at 37° C., because of a failure in appropriate organelle segregation at the higher temperature (mitochondria are not put into daughter cells). In such a temperature-sensitive mutant, the daughter cells bud off from the mother cell and die at the non-permissive temperature; the dead daughter cells remain near the mother cell. Therefore, each mother cell grown at the non-permissive temperature generates a microcolony of N cells, where N is equal to the number of generations in the life span of the mother cell. Mutant strains will display microcolonies wherein the number of cells is greater than N.

To isolate cells having an extended life span, cells are plated at the permissive temperature. A sample of cells from each colony is then transferred to a plate to be grown at the non-permissive temperature. Microcolonies with cell number greater than N are indicative of mutants having an extended life span; cells from the colonies which have been identified as mutant can be selected from the plates grown at the permissive temperature. Alternatively, cells are plated directly at the non-permissive temperature, and grown for a period of time greater than the life span as measured by time necessary for one cell division, multiplied by the number of divisions, or generations, in the life span. If desired, the yeast cells may be sampled at regular time intervals in order to monitor the plating efficiency of the cells; the efficiency will drop precipitously after the chronological life span has passed. After this time, the plates are shifted back to the permissive temperature. Only longer-lived cells will grow after the temperature shift.

The above-described methods for isolating cells with a longer life span can be employed to confirm or test the ability of agents, identified by their ability to inhibit the replication and/or accumulation of DNA circles, to alter the life span of an organism. For example, agents which have been identified by methods described herein as inhibiting the replication and/or accumulation of rDNA circles in an organism can be assessed to determine their ability to extend the life span of treated cells. In one embodiment of the current invention, the cells of interest, for which the life span is known or has been calculated, are exposed to or treated with an agent to be tested, e.g., an agent which inhibits the replication and/or accumulation of rDNA circles in a cell. The cell samples thus exposed or treated are then examined for longer-lived colonies, using any of the methods described above or other appropriate methods. Colonies exhibiting a longer life span in the presence of the agent than in the absence of the agent are indicative of the ability of the agent to increase life span, or to postpone senescence. Appropriate agents to be tested can include drugs, small molecules, peptides, oligonucleotides, antibodies, and genes encoding proteins that increase life span.

Alternatively, agents identified as inhibiting the replication and/or accumulation of rDNA circles can be assessed to determine their ability to extend life span at the organismal level. For example, a mammal can be treated with an agent identified by its ability to inhibit the replication and/or accumulation of DNA circles, and the mammal can be assessed for the slowing of the normal phenotypes of aging, such as hair loss, graying of hair, osteoporosis, cataracts, atherosclerosis, loss of skin elasticity and a propensity for certain cancers.

Compounds identified by the assays described herein which extend life span as described above, can be used to extend the life span of cells, e.g., mammalian cells including human cells. For example, cells to be treated can be contacted with the identified compound, thereby extending their life span relative to untreated cells.

The present invention also pertains to pharmaceutical compositions comprising compounds or agents described herein. For instance, a compound of the present invention (e.g., a life-span extending agent) can be formulated with a physiologically acceptable vehicle to prepare a pharmaceutical composition. These compounds can be administered, e.g., parenterally, as a solution, alone or in combination with other compounds dissolved in an acceptable carrier, preferably an aqueous carrier. A variety of appropriate aqueous carriers are known to the skilled artisan, including water, buffered water, buffered saline, polyols (e.g., glycerol, propylene glycol, liquid polyethylene glycol), dextrose solution and glycine. These compositions can optionally contain pharmaceutically acceptable auxiliary substances as required to approximate physiological conditions such as pH adjusting and buffering agents and toxicity adjusting agents, for example, sodium acetate, sodium chloride, potassium chloride, calcium chloride and sodium lactate. The optimum concentration of the active ingredient(s) in the chosen vehicle can be determined empirically, according to procedures well known to the skilled artisan, and will depend on the ultimate pharmaceutical formulation desired.

The present invention further relates to an agent, compound or nucleic acid molecule as described herein for use in therapy (including prophylaxis) or diagnosis, and to the use of such an agent, compound or nucleic acid molecule for the manufacture of a medicament for the treatment of an age-related disorder or for the inhibition of aging as described herein.

A variety of routes of administration are possible including, but not limited to, oral, sublingual, intraocular, dietary, topical, parenteral (e.g., intravenous, intraarterial, intramuscular, subcutaneous injection), inhalation (e.g., intrabronchial, intranasal or oral inhalation, intranasal drops), routes of administration, depending on the disease or condition to be treated. Other suitable methods of introduction can also include rechargeable or biodegradable devices and slow release polymeric devices. The pharmaceutical compositions of this invention can also be administered as part of a combinatorial therapy with other agents.

Formulation (e.g., solution, emulsion, capsule) of a compound to be administered will vary according to the route of administration selected. An appropriate composition comprising the compound to be administered can be prepared in a physiologically acceptable vehicle or carrier. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils. Intravenous vehicles can include various additives, preservatives, or fluid, nutrient or electrolyte replenishers (See, generally, *Remington's Pharmaceutical Science*, 16th Edition, Mack, Ed. 1980). For inhalation, the compound can be solubilized and loaded into a suitable dispenser for administration (e.g., an atomizer, nebulizer or pressurized aerosol dispenser).

As described herein, it has been determined that there is a mouse homolog of Sgs1p and WRN (Imamura et al., *Genomics* 41:298–300 (1997); this gene is referred to herein as mWRN. Accordingly, the invention pertains to an isolated nucleotide sequence (nucleic acid molecule) encoding mWRN. In a particular embodiment, the nucleic acid sequence encoding mWRN has the nucleotide sequence of SEQ ID NO: 5. As appropriate, nucleic acid molecules of the present invention can be RNA, for example, MRNA, or DNA, such as DNA and genomic DNA. DNA molecules can be double-stranded or single-stranded; single stranded RNA or DNA can be either the coding, or sense, strand or the non-coding, or antisense, strand. Preferably, the nucleic acid molecule comprises at least about 25 nucleotides, more preferably at least about 50 nucleotides, and even more preferably at least about 200 nucleotides. The nucleotide sequence can be only that which encodes at least a fragment of the amino acid sequence of the mWRN protein; alternatively, the nucleotide sequence can include at least a fragment of the mWRN amino acid coding sequence along with additional non-coding sequences such as introns and non-coding 3' and 5' sequences (including regulatory sequences, for example). Additionally, the nucleotide sequence can be fused to a marker sequence, for example, a sequence which encodes a polypeptide to assist in isolation or purification of the protein or polypeptide. Such sequences include, but are not limited to, those which encode a glutathione-S-transferase (GST) fusion protein and those which encode a hemaglutin A (HA) peptide marker from influenza.

The term "isolated" is used herein to indicate that the material in question exists in a physical milieu distinct from that in which it occurs in nature. For example, the isolated protein of the invention may be substantially isolated with respect to the complex cellular milieu in which it naturally occurs. In some instances, the isolated material will form part of a composition (for example, a crude extract containing other substances), buffer system or reagent mix. In other circumstances, the material may be purified to essential homogeneity from other transcribed sequences (as in a cDNA or RNA library), for example as determined by PAGE or column chromatography such as HPLC. Thus, an isolated gene or nucleotide sequence can include a gene or nucleotide sequence which is synthesized chemically or by recombinant means. Thus, recombinant DNA contained in a vector are included in the definition of "isolated" as used herein. Also, isolated nucleotide sequences include recombinant DNA molecules in heterologous host cells, as well as partially or substantially purified DNA molecules in solution. In vivo and in vitro RNA transcripts of the DNA molecules of the present invention are also encompassed by "isolated"0 nucleotide sequences. Such isolated nucleotide sequences are useful in the manufacture of the encoded protein, as probes for isolating homologous sequences (e.g., from other mammalian species), for gene mapping (e.g., by in situ hybridization with chromosomes), or for detecting expression of the MiWRN gene in tissue (e.g., human tissue), such as by Northern blot analysis.

The present invention also pertains to nucleotide sequences which are not necessarily found in nature but which encode mWRN. Thus, DNA molecules which comprise a sequence which is different from the naturally-occurring nucleotide sequence but which, due to the degeneracy of the genetic code, encode mWRN protein of the present invention are the subject of this invention. The invention also encompasses variations of the nucleotide sequences of the invention, such as those encoding portions, analogues or derivatives of mWRN. Such variations can be naturally-occurring, such as in the case of allelic variation, or non-naturally-occurring, such as those induced by various mutagens and mutagenic processes. Included variations include, but are not limited to, addition, deletion and substitution of one or more nucleotides which can result in conservative or non-conservative amino acid changes, including additions and deletions. Preferably, the nucleotide or amino acid variations are silent or conserved, respectively; that is, they do not alter the characteristics or activity of mWRN.

The invention described herein also relates to fragments of the isolated nucleic acid molecules described above. For example, fragments which encode antigenic regions of mwRN are useful. The term "fragment" is intended to encompass a portion of a nucleotide sequence described herein which is from at least about 25 contiguous nucleotides to at least about 50 contiguous nucleotides or longer in length; such fragments are useful as probes, e.g., for diagnostic methods and also as primers. Particularly preferred primers and probes selectively hybridize to the nucleic acid molecule encoding mWRN described herein.

The invention also pertains to nucleotide sequences which hybridize under high stringency hybridization conditions (e.g., for selective hybridization) to a portion of a nucleotide sequence described herein or its complement and encode a protein or polypeptide which functions in aging. Appropriate stringency conditions are known to those skilled in the art or can be determined with reference to standard texts such as *Current Protocols in Molecular Biology*, John Wiley & Sons, N.Y. (1989), 6.3.1–6.3.6. Such hybridizable nucleotide sequences are useful as probes and primers for diagnostic applications.

The invention also relates to nucleotide sequences which share at least about 85% sequence identity with the nucleotide sequence encoding mWRN, preferably at least about 90% sequence identity, and more preferably at least about 95% sequence identity with said mWRN. Sequence identity can be determined using a suitable program, such as the Blastx program (Version 1.4), using appropriate parameters, such as default parameters. In one embodiment, parameters for Blastx search are scoring matrix BLOSUM62, W=3. In another embodiment, the invention pertains to a nucleic acid sequence which is different from the naturally-occurring nucleic acid molecule but which, due to the degeneracy of the genetic code, encodes mWRN or a portion thereof.

Accordingly, the invention pertains to nucleotide sequences which have a substantial identity with the nucleotide sequences described herein. Particularly preferred in this instance are nucleotide sequences encoding polypeptides having at least one activity of mWRN. For example, preferred nucleotide sequences encoding a polypeptide having the same or similar biological activity as mWRN and nucleotide sequences encoding a polypeptide with the same or similar immunogenic or antigenic properties as mWRN are within the scope of the invention, as well as nucleotide sequences which hybridize to DNA which encodes mWRN or a protein with mWRN activity. These nucleotide sequences are considered to be "active derivatives" of mWRN. As used herein, activities of mWRN include, but are not limited to, catalytic activity, binding function, antigenic function and oligomerization function.

This invention also pertains to an isolated protein or polypeptide which is mWRN. In a particular embodiment, the protein has the amino acid sequence of SEQ ID NO: 6. The mWRN protein or polypeptide of the invention can be partially or substantially purified (e.g., purified to homogeneity), and/or is substantially free of other proteins. According to the invention, the amino acid sequence of the polypeptide can be that of the naturally-occurring protein or can comprise alterations therein. Such alterations include conservative or non-conservative amino acid substitutions, additions and deletions of one or more amino acids. Such altered or mutant proteins should exhibit at least one activity of mWRN, i.e., the altered or mutant protein should be an active derivative of the naturally-occurring protein. For example, the mutation(s) can preferably preserve the three dimensional configuration of the binding and/or catalytic site of the native protein. The presence or absence of mWRN activity or activities can be determined by various functional assays as described herein. Moreover, amino acids which are essential for the function of mWRN can be identified by methods known in the art. Particularly useful methods include site-directed mutagenesis and alanine-scanning mutagenesis (for example, Cunningham and Wells, *Science* 244:1081–1085 (1989)), crystallization and nuclear magnetic resonance. The altered polypeptides produced by these methods can be tested for particular biologic activities, including immunogenicity and antigenicity.

Specifically, appropriate amino acid alterations can be made on the basis of several criteria, including hydrophobicity, basic or acidic character, charge, polarity, size, the presence or absence of a functional group (e.g., —SH or a glycosylation site), and aromatic character. Assignment of various amino acids to similar groups based on the properties above will be readily apparent to the skilled artisan; further appropriate amino acid changes can also be assessed with reference to Bowie et al. (*Science* 247:1306–1310(1990)).

The mWRN polypeptide can also be a fusion protein comprising all or a portion of the mWRN amino acid sequence fused to an additional component. Additional components, such as radioisotopes and antigenic tags, can be selected to assist in the isolation or purification of the polypeptide or to extend the half life of the polypeptide; for example, a hexahistidine tag would permit ready purification by nickel chromatography.

Also included in the invention are polypeptides which are substantially identical to mWRN. However, polypeptides exhibiting lower levels of identity are also useful, particular if they exhibit high, e.g., at least about 40%, identity in one or more particular domains of the protein. For example, polypeptides sharing high degrees of identity in domains necessary for particular activities are included herein.

Polypeptides described herein can be isolated from naturally-occurring sources, chemically synthesized or recombinantly produced, and all such polypeptides are encompassed the term "isolated" protein or polypeptide. Polypeptides or proteins of the present invention can be used as a molecular weight marker on SDS-PAGE gels or on molecular sieve gel filtration columns using art-recognized methods.

The invention also provides expression vectors containing a nucleic acid sequence encoding a polypeptide which is mWRN, operably linked to at least one regulatory sequence. Many such vectors are commercially available, and other suitable vectors can be readily prepared by the skilled artisan. "Operably linked" is intended to mean that the nucleotide sequence is linked to a regulatory sequence in a manner which allows expression of the nucleic acid sequence in an appropriate host cell. Regulatory sequences are art-recognized and are selected to produce a polypeptide which is mWRN. Accordingly, the term "regulatory sequence" includes promoters, enhancers, and other expression control elements which are described, for example, in Goeddel, *Gene Expression Technology: Methods in Enzymology* 185, Academic Press, San Diego, Calif. (1990). For example, the native regulatory sequences or regulatory sequences native to the transformed host cell can be employed. It should be understood that the design of the expression vector may depend on such factors as the choice of the host cell to be transformed and/or the type of protein desired to be expressed. For instance, the polypeptides of the present invention can be produced by ligating the gene, or a portion thereof, into a vector suitable for expression in either prokaryotic cells, eukaryotic cells or both (see, for example, Broach, et al., *Experimental Manipulation of Gene Expression*, ed. M. Inouye (Academic Press, 1983) p. 83; *Molecular Cloning: A Laboratory Manual*, 2nd Ed., ed. Sambrook et al. (Cold Spring Harbor Laboratory Press, 1989) Chapters 16 and 17). Typically, expression constructs will contain one or more selectable markers, including, but not limited to, the gene that encodes dihydrofolate reductase and the genes that confer resistance to neomycin, tetracycline, ampicillin, chloramphenicol, kanamycin and streptomycin resistance.

Prokaryotic and eukaryotic host cells transfected by the described vectors are also provided by this invention. For instance, cells which can be transfected with the vectors of the present invention include, but are not limited to, bacterial cells such as *E. coli* (e.g., *E. coli* K12 strains), Streptomyces, Pseudomonas, *Serratia marcescens* and *Salmonella typhimurium*, insect cells (baculovirus), including Drosophila, fungal cells, such as yeast cells, plant cells and mammalian cells, such as Chinese hamster ovary cells (CHO), and COS cells.

A nucleotide sequence of mWRN described herein can be used to produce a recombinant form of the protein via microbial or eukaryotic cellular processes. Ligating the polynucleotide sequence into a gene construct, such as an expression vector, and transforming or transfecting the vector into hosts, either eukaryotic (yeast, avian, insect, plant or mammalian) or prokaryotic (bacterial cells), are standard procedures used in producing other well known proteins. Similar procedures, or modifications thereof, can be employed to prepare recombinant proteins according to the present invention by microbial means or tissue-culture technology. Accordingly, the invention pertains to the production of mWRN proteins or polypeptides by recombinant technology.

The proteins and polypeptides of the present invention can be isolated or purified (e.g., to homogeneity) from recombinant cell culture by a variety of processes. These include, but are not limited to, anion or cation exchange chromatography, ethanol precipitation, affinity chromatography and high performance liquid chromatography (HPLC). The particular method used will depend upon the properties of the polypeptide and the selection of the host cell; appropriate methods will be readily apparent to those skilled in the art.

The present invention also relates to antibodies which bind mWRN. For instance, polyclonal and monoclonal antibodies, including non-human and human antibodies, humanized antibodies, chimeric antibodies and antigen-binding fragments thereof (*Current Protocols in Immunology*, John Wiley & Sons, N.Y. (1994); EP Application 173,494 (Morrison); International Patent Application WO86/01533 (Neuberger); and U.S. Pat. No. 5,225,539 (Winters)) which bind to mWRN are within the scope of the invention. A mammal, such as a mouse, rat, hamster or rabbit, can be immunized with an immunogenic form of the protein (e.g., mWRN or a peptide comprising an antigenic fragment of mWRN which is capable of eliciting an antibody response). Techniques for conferring immunogenicity on a protein or peptide include conjugation to carriers or other techniques well known in the art. The protein or polypeptide can be administered in the presence of an adjuvant. The progress of immunization can be monitored by detection of antibody titers in plasma or serum. Standard ELISA or other immunoassays can be used with the immunogen as antigen to assess the levels of antibody.

Following immunization, anti-peptide antisera can be obtained, and if desired, polyclonal antibodies can be isolated from the serum. Monoclonal antibodies can also be produced by standard techniques which are well known in the art (Kohler and Milstein, *Nature* 256:495–497 (1975); Kozbar et al., *Immunology Today* 4:72 (1983); and Cole et al., *Monoclonal Antibodies and Cancer Therapy*, Alan R. Liss, Inc., pp. 77–96 (1985)). The term "antibody" as used herein is intended to include fragments thereof, such as Fab and $F(ab)_2$. Antibodies described herein can be used to inhibit the activity of mWRN, particularly in vitro and in cell extracts, using methods known in the art. Additionally, such antibodies, in conjunction with a label, such as a radioactive label, can be used to assay for the presence of the expressed protein in a cell from, e.g., a tissue sample, and can be used in an immunoabsorption process, such as an ELISA, to isolate the protein. Tissue samples which can be assayed include human tissues, e.g., differentiated and non-differentiated cells. Examples include bone marrow, thymus, kidney, liver, brain, pancreas, fibroblasts and epithelium.

A more complete understanding of the role of various genes and proteins in aging can be obtained by studying the effects of these genes and proteins directly in a mammal (i.e., an in vivo system). Accordingly, mammals have been produced as described herein that have altered levels of expression of certain genes; these mammals are also subjects of the present invention. In particular, as described herein, a "knockout" mouse has been produced in which expression of an endogenous gene, mWRN, has been suppressed through genetic manipulation.

Preparation of a knockout mammal requires first introducing a nucleic acid construct used to suppress expression of a particular gene into an undifferentiated cell type (e.g., an embryonic stem cell) or a fertilized egg. This cell is then injected into a mammalian embryo, where it will be integrated into the developing embryo. The embryo is then typically implanted into a foster mother for the duration of gestation. Knockout mice in which various genes have been suppressed are known in the art (Pfeffer et al., *Cell* 73:457–467 (1993); Fung-Leung et al., *Cell* 65:443–449 (1991); U.S. Pat. No. 5,616,491 (Mak et al.)). The methodology for producing the knockout animals described herein is known to the skilled artisan.

The invention also pertains to non-human transgenic animals and their progeny, such as a mouse and its progeny, having a suppressed level of expression of the mWRN gene. The invention also relates to embryonic stem cell lines containing a mWRN knockout construct. As used herein, the term "knockout" refers to partial or complete suppression of the expression of at least a portion of a protein encoded by an endogenous DNA sequence in a cell. The term "knockout construct" refers to a nucleic acid sequence that is designed to decrease or suppress expression of a protein encoded by endogenous DNA sequences in a cell. The term "progeny" refers to all future generations derived and descending from a particular mammal, i.e., a mammal containing a knockout construct inserted into its genomic DNA. Thus, progeny of any successive generation are included herein such that the progeny, the F1, F2, F3 (and so on indefinitely) generations are included in this definition. As used herein, the term "suppress" is intended to encompass both complete and partial suppression of gene expression, including reduced expression as compared with the wild type or naturally-occurring gene.

The nucleic acid sequence used as the knockout construct is typically comprised of DNA from some portion of the gene (e.g., exon sequence, intron sequence and/or promoter sequence) and a marker sequence used to detect the presence of the knockout construct in the cell. The marker sequence is typically a sequence that encodes a protein that confers a detectable trait on the cell, such as an antibiotic resistance gene or an assayable enzyme not typically found in the cell. The knockout construct is inserted into a cell and integrates with the genomic DNA of the cell in such a position as to prevent or interrupt transcription of the native DNA sequence. Preferably the nucleic acid sequence of the knockout construct is inserted into a region of the native DNA sequence and/or the promoter region of the gene so as to decrease or prevent expression of that gene in the cell as compared to the wild type or naturally-occurring sequence of the gene.

In another embodiment, the invention relates to a method of screening a compound, such as a compound identified as having the ability to inhibit the replication and/or accumulation of DNA circles, for the ability to affect or alter life span, comprising administering the compound to a mouse, e.g., a mouse with a suppressed level of mWRN expression, and determining whether the mouse's life span is different from (longer or shorter than) that of a comparable mouse to which the compound has not been administered (a control mouse). As used herein, "ability to affect life span" is intended to encompass both the ability to enhance and inhibit life span. Compounds can be screened to determine their ability to extend or shorten life span; of particular interest are compounds which are able to extend life span. The present invention also relates to novel agents or compounds identified by the assay described above. Agents identified by the assay described herein may enhance or inhibit aging, and the invention also pertains to the use of compounds identified as described herein, particularly to inhibit aging at the cellular or organismal level.

Screening for useful compounds requires administering the compound to be tested over a range of doses to the mouse, and assaying at various time points for the effect on life span. Such assays include, for example, assaying for increased or decreased levels of expression of particular genes involved in aging, and measuring the life span of the treated mouse. A mammal of the present invention can be used to screen a variety of compounds, either alone or in combination, to determine whether partial or total enhancement or inhibition of aging results. Enhancement of aging, or an increase in aging relative to a control, indicates that the agent shortens life span. Similarly, inhibition of aging, or a decrease in aging relative to a control, indicates that the agent extends life span. In addition, mammals of the present invention are useful for evaluating the development of the immune system, and for studying the effects of particular gene mutations.

Examples described herein are offered for the purpose of illustrating the present invention and are not to be construed to limit the scope of this invention. The teachings of all references cited herein are hereby incorporated herein by reference.

EXAMPLES

Premature Aging of sgs1 Mutants

Life span analysis of the wild type *S. cerevisiae* W303-1A (MATa ade2-1 can1-100 his3-11,15 leu2-3,112 trp1-1 ura3-1, from R. Rothstein) and isogenic mutant derivatives, sgs1::HIS3, ada1::hisG, and hap5::hisG were determined by the removal of daughters from at least 40 virgin mothers by micromanipulation until senescence of the mother cell occurred (Müller et al., *Aging Dev.* 12:47 (1980)). As described herein, it was determined that the average life span of sgs1 cells (9.5 divisions) is about 40% that of the wild type strain (24.5 divisions) (FIG. 1A). The maximum life span of sgs1 cells was similarly reduced compared to wild type (18 versus 40 divisions). This shortening is unlikely to be due to a general sickness, since the growth rate of sgs1 strains is indistinguishable from the wild type strain.

Figure 2A:
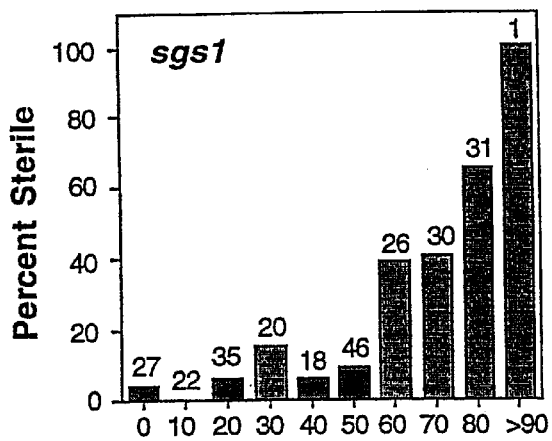
FIGS. 2A–2D illustrate that mutant sgs1 cells age prematurely. Cells of various ages were scored for their ability to undergo cell cycle arrest and schmooing in response to the yeast mating pheromone, α-factor. The number of cells in each data set for each age group are shown above the bar.
Figure 2B:
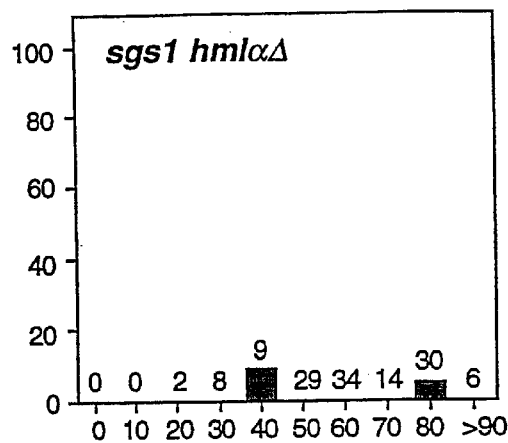

To determine whether the sgs1 mutation indeed aged prematurely and did not simply die early, the age-specific phenotype of sterility was examined. Cells were scored at various stages of their life span for their ability to respond to the mating pheromone, α-factor. After 4 hours of α-factor challenge, cells were moved to fresh medium to complete their life span. Life span is not affected by deletion of HML (Smeal et al., *Cell* 84:633 (1996)). Cells which failed to respond or divide after α-factor challenge were excluded from the data set. Disruption plasmids pCW9-1, and pDM212 (McNabb et al., *Genes Dev.* 9:47 (1995)), pADA1KO (Horiuchi et al., *Mol. Cell. Biol.*, in press (1997)) were used to create hm1αΔ::LEU2, hap5::hisG and ada1::hisG strains, respectively (W303-1A background). As described herein, it was determined that in the sgs1 mutant, young cells that had completed less than 50% of their life span were almost always fertile (FIG. 2A). However, over 60% of cells in the last one-fifth of their life span were sterile. As observed previously for wild type cells, this sterility is due to a loss of silencing, since deletion of HMLα reduces the frequency of sterility in a MATa strain to almost zero (FIG. 2B).

Figure 1B:
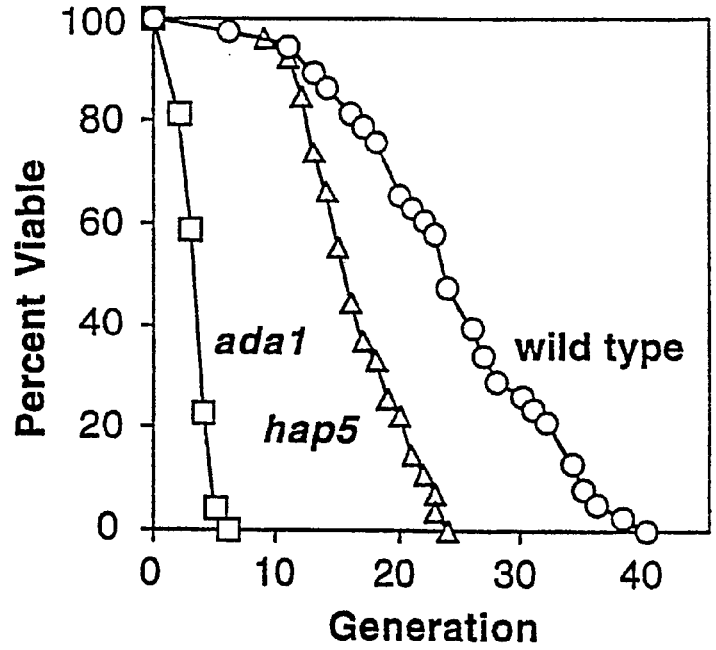
Figure 2C:
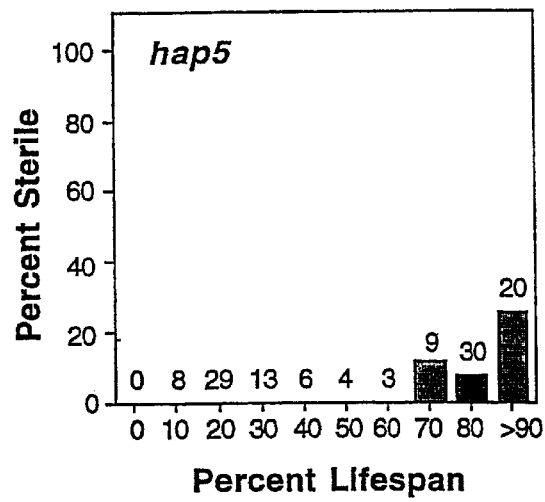
Figure 2D:
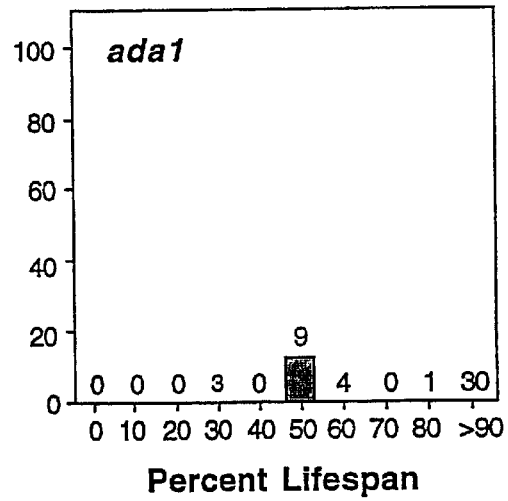

Because it was important to show that the sterility of old sgs1 cells was specific to this mutant, other mutant strains were examined to determine whether or not a short life span also led to premature sterility. After examination of a number of strains that did not affect life span, it was determined that mutations in the transcriptional activator HAP5 (McNabb et al., *Genes Dev.* 9:47 (1995)) and in the coactivator ADA1 (Horiuchi et al., *Mol. Cell. Biol.*, in press (1997)) significantly shortened life span in the isogenic W303 strain background (FIG. 1B). However, in contrast to the sgs1 mutant, neither the hap5 nor the ada1 strains became sterile at a high frequency as they grew older (FIGS. 2C and 2D). Rather, the frequency of sterile cells from these strains was proportional to the fraction of the wild type life span that cells had completed. Thus, sterility is an aging-specific phenotype that occurs prematurely in short-lived sgs1 mutants.

Concentration of Sgs1p in the Nucleolus

The remarkable similarity between the effects of the SGS1 mutation in yeast and WRN mutations in humans prompted a molecular analysis of the yeast gene product with a view to gaining some insight into the function of the human protein. In order to raise antibody to Sgs1p, the carboxyl terminus (residues 1071 to 1447) was fused to a 6 histidine tag and expressed in *E. coli*. Purified recombinant protein was injected into chickens and anti-Sgs1p IgY was obtained by affinity purification using recombinant protein. The C-terminal of Sgs1 was amplified by PCR (from +3208 to +4344) using the oligonucleotides GGGGGGGATC- CAATTGTAGAAATAGCGCCAACG (SEQ ID NO: 1) and GGGGGGAGCTCTCACTTTCTTCCTCTGTAGTGA (SEQ ID NO: 2). The product was cut with BamHI and SacI then ligated to pET-28a(+) (Novagen Corp., Madison, Wis.) cut with the same enzymes to create pET28N-SGS1. BL21 (DE3) cells (Studier, *J. Mol. Biol.* 189:113 (1991)) were transformed with pET28N-SGS1 and grown in 2 liters incomplete medium to an $OD_{600}$ of 1. Expression was induced with 1 mM IPTG for 4 hours; cells were resuspended for 1 hour in lysis buffer (20 mM Tris-HCl [pH 7.9], 500 mM NaCl, 6 M guanidine-HCl, 5 mM imidazole). Debris was spun down (5,000×g, 20 minutes) and the supernatant was passed through a Ni-NTA agarose column (10 ml bed volume), pre-equilibrated with wash buffer (20 mM Tris-HCl [pH 7.9], 500 mM NaCl, 6 M urea, 20 mM imidazole). The column was washed with 5 volumes wash buffer, and protein was eluted with elution buffer (20 mM Tris-HCl [pH 7.9], 500 mM NaCl, 6 M urea, 300 mM imidazole). The antibody recognized 0.1 ng of recombinant protein and Sgs1p in yeast extracts.

Sgs1p was visualized by indirect immunofluorescence of fixed yeast cells stained with the purified antibody and FITC-conjugated anti-chicken IgY as previously described (Kennedy et al., *Cell* 89:381 (1997))- *E. coli* recombinant 6 histidine-tagged Sgs1p (amino acids 1071 to 1447) was affinity purified using Ni-NTA agarose, 200 μg of which was injected into chickens; 100 μg of protein was used for subsequent boosts. Anti-Sgs1p IgY molecules were purified from chicken serum by affinity purification using recombinant Sgs1p. Sgs1p staining (green) was predominantly in the nucleus, which is stained with DAPI (blue); a concentration of the staining on one side of each nucleus was also observed. Co-staining cells for yeast Nop1p (red), an abundant nucleolar protein (Henriquez et al., *J. Biol. Chem.* 265:2209 (1990); Tollervey et al., EMBO J. 10:573 (1997)), clearly demonstrated that this concentration of Sgs1p corresponded to the nucleolus (yellow in a merged image).

SGS1 was amplified by PCR (from +4 to +4344) using the oligonucleotides GGGGGGGATCCAGTGACGAAGC-CGTCACATAACTTA (SEQ ID NO: 3) and GGGGGGCG-GCCGCTTATCACTTTCTTCCTCTGTAGTGACC (SEQ ID NO: 4). The product, cut with BamHI and NotI, was ligated to the galactose-inducible promoter of yCPIF15 (Foreman and Davis, Gene 144:63 (1994)). Overexpression of GALp-SGS1 was induced by growing for 4 hours in YPGal (10 g/l yeast extract, 20 g/l bactopeptone, 2 g/l galactose), and confirmed by Western blot using anti-HA mAb. Images were acquired using the CELLScan imaging system and processed as previously described (Kennedy et al., *Cell* 89:381 (1997)).

Fragmentation of the Nucleolus in Old Cells

Since Sgs1p localized predominately to the nucleolus, and movement of Sir proteins to the nucleolus results in an extension of life span, it seemed possible that nucleolar changes might be observed during the life span of sgs1 cells- Thus, old sgs1 cells were obtained by magnetic sorting as described in Smeal et al. (*Cell* 84:633 (1996)). By counting bud scars it was determined that, on average, the cells had divided 9 (±2 standard deviations) times, which is approximately the average life span of the strain.

Once again, antibodies directed against Nop1p were used to examine the overall structure of the nucleolus. SIR3 was disrupted with pDM42. Starved cells were obtained by growing a culture first in YPD medium to stationary phase, then in 2.4 g/l yeast nitrogen base without amino acids for 12 hours. As observed for young wild type cells (Henriquez et al.,*J. Biol. Chem.* 265:2209 (1990)), the nucleoli of young sgs1 cells were well defined crescent-shaped structures occupying about 20% of the nucleus. Strikingly, in about 50% of the old sgsi cells, the nucleolus was fragmented into several bodies which occupied a large fraction of the nucleus (average bud scar count, ABSC, of magnetic sort: 9±2 standard deviations). In the fraction of old cell nuclei in which nucleolar fragmentation was not observed, a substantial enlargement of the structure was evident. Interestingly, in young wild type yeast cells expressing SGS1 at high levels, a similar pattern of nucleolar fragmentation was observed. These mininucleolar bodies (Oakes et al., *Mol. Cell. Biol.* 13:2441 (1993)) structurally resemble the precursors of the interphase nucleolus of higher eukaryotes (Stevens, *J. Cell Biol.* 13:2455 (1965)).

To address the question of whether the enlargement and fragmentation of the nucleolus is due to scaling of a normal aging phenotype, or is merely a consequence of the sgs1 mutation per se, very old wild type cells which had divided an average of 26 times, approximately the average life span of the strain, were obtained. Staining for Nop1p revealed that a substantial fraction (about 45%) of these had enlarged or fragmented nucleoli, similar to the changes seen in the old sgs1 cells. Thus, fragmentation is a novel feature of aging that occurs in wild type as well as sgs1 cells. Consistent with a link between normal aging and fragmentation of the nucleolus, ada1 mutants, which die early rather than age prematurely, did not display fragmentation of the nucleolus in young or old cells.

To determine whether enlargement and fragmentation of the nucleolus might be a response to a reduction in protein synthesis, young wild type cells were starved and nucleolar staining was carried out. It was observed that the nucleoli did not enlarge or fragment, rather, they were reduced to approximately 25% the size of wild type nucleoli with a more rounded appearance.

Redistribution of Sir3p to Nucleolar Bodies in Old sgs1 Mutants

A key molecular signature of aging in yeast is redistribution of the Sir proteins to the nucleolus in old cells. This redistribution, if observed for sgs1 cells, would provide the most compelling evidence that mutation of SGS1 resulted in premature aging. It was of particular interest to determine whether the complex would redistribute to the satellite nucleolar bodies in old cells with fragmented nucleoli. Indirect immunofluorescence was performed in young and old sgs1 mutant cells using rabbit anti-Sir3p. Nop1p was visualized with Cy3-conjugated anti-mouse IgG (red); DNA was stained with DAPI (blue); Sir3p was visualized with FITC-conjugated goat anti-rabbit IgG (green). Overlap of Sir3p and Nop1p staining is observed as yellow. In young cells, Sir3p staining showed characteristic telomere spots (Gotta et al., *EMBO J.* in press (1997); Palladino et al., *Cell* 75:543 (1993)) which were separate from the nucleolus. However, in old sgs1 cells Sir3p staining was predominantly nucleolar. In old cells with fragmented nucleoli, Sir3p staining coincided with most or all nucleolar bodies.

Nucleolar Enlargement and Fragmentation Do Not Require the Sir Protein Complex

Nucleolar enlargement and fragmentation could either represent a cause of aging, or, alternatively, be a response to aging which actually promotes longevity. If fragmentation of the nucleolus is a response in old cells that promotes longevity, it might be caused by redistribution of the Sir complex to the nucleolus. A test of this hypothesis is that fragmentation would not occur in a sir null mutant. Thus, old sgs1 sir3 cells were sorted and Nop1p staining was performed as described above. Clearly, nucleolar fragmentation occurred at the same high level in the double mutant, showing that the Sir complex is not required for fragmentation.

It was still possible that nucleolar enlargement and fragmentation was part of a longevity mechanism, but did not require Sir-protein redistribution for its formation. To test further whether nucleolar fragmentation could be part of a longevity response mechanism, SGS1 wild type strains, which were either SIR3 (wild type) or sir3, were grown for 12 divisions and sorted for old cells. Young wild type W303-1A and an isogenic sir3 mutant were labeled with biotin, grown for 17 hours and sorted back, as previously described (Smeal et al., Cell 84:633 (1996)). At this age, sir3 cells are approaching senescence because of their shorter life span, but the majority of wild type cells are not. Nop1p staining showed that a substantial fraction of the nucleoli in the sir3 mutant were either enlarged or fragmented (38% and 19%, respectively), a proportion much higher than in the age-matched wild type (12% and 6%, respectively). This finding suggests that the redistribution of the Sir complex to the nucleolus (which can occur in the wild type but not sir3 mutant) represses nucleolar fragmentation. These results are thus consistent with the model that a process leading to nucleolar fragmentation is one of the causes of yeast aging.

Preparation of a mWRN Knockout Mouse

In order to generate constructs necessary to inactivate the mWRN gene in murine ES cells, a mouse genomic lambda phage library derived from the 129 strain was screened with a hybridization probe corresponding to the full-length mWRn cDNA. Seven clones were obtained and plaque-purified. Two clones were chosen for more detailed analysis because hybridization using different probes in the mWRN cDNA indicated that they were the farthest 5' regions obtained in this screen and that they contained fragments of the helicase domain.

These genomic fragments were subsequently transferred from lambda phage to the bacterial vector pBR322 for ease of analysis via cloning into the SalI site in this vector, and they were then extensively mapped with restriction enzymes. These clones proved to overlap extensively. DNA sequencing revealed the presence of an exon encompassing the 3' region of the helicase domain in a 4.4 kB HindIII-BamHI fragment. A suitable vector was constructed in the plasmid pSL1190, with a βgeo (β-galactosidase/neomycin$^r$ fusion gene) cassette replacing the HindIII-BamHI fragment. Splicing to the next exon is predicted to introduce a frameshift mutation.

Figures 3A, 3B:
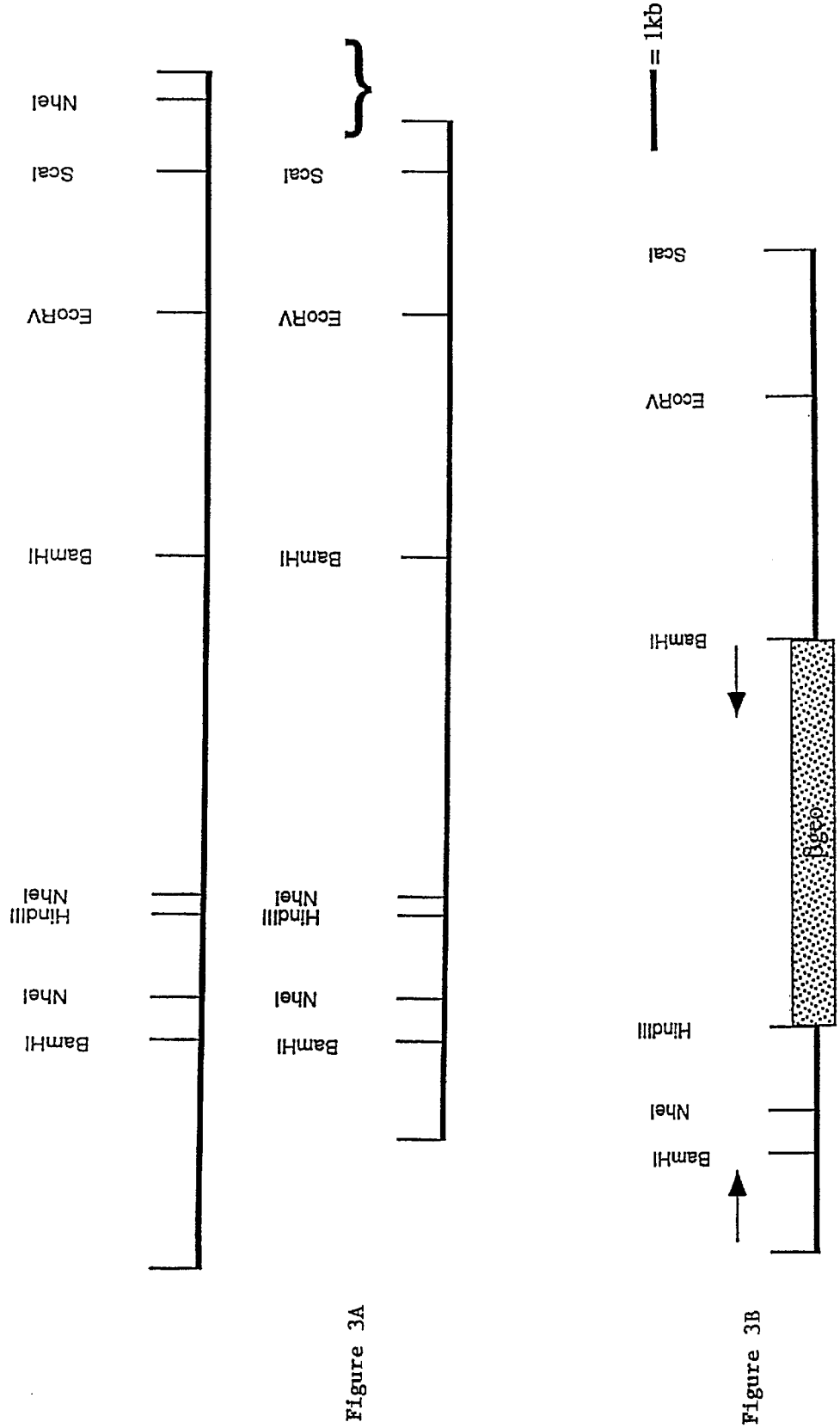
FIGS. 3A and 3B show mWRN genomic clones and targeting construct.

This construct was introduced into J1 ES cells by electroporation and neomycin-resistant colonies subcloned. Eighty-eight clones have been examined for appropriate targeting using a hybridization probe lying outside the construct. This probe consists of a ScaI/NheI fragment at the 3' end of one of the genomic fragments and distinguishes between the wild-type and mutant alleles in an NheI digest. Among the eighty-eight clones screened by Southern blot, eleven clones had undergone the appropriate integration event. Three of these clones have been expanded and injected into C57BL/6 and BALB/c blastocysts, and these blastocysts surgically implanted into pseudopregnant Swiss Webster outbred mothers. Chimeric mice were obtained from all three cell lines and were distinguished by their agouti coats. These chimeras were bred with balb/c and C57BL/6 mice and heterozygotes were obtained from two of three original clones. These heterozygotes or their offspring were intercrossed to obtain homozygotes (FIGS. 3A and 3B).

EQUIVALENTS

Those skilled in the art will recognize, or be able to ascertain, using no more than routine experimentation, many equivalents to the specific embodiments of the invention described herein. Such equivalents are intended to be encompassed by the following claims:

We claim:

1. A method of identifying an agent which inhibits the replication or accumulation of ribosomal DNA circles in a yeast cell, comprising the steps of:
   a) transforming a yeast cell deficient in a gene encoding a protein necessary for growth with a plasmid comprising a ribosomal DNA autonomously replicating sequence and a marker gene encoding the protein necessary for growth, to produce a transformed yeast cell;
   b) identifying a transformed yeast cell in which the plasmid has stably integrated into the ribosomal DNA genome and a transformed yeast cell in which the plasmid has not integrated into the ribosomal DNA genome;
   c) incubating the transformed yeast cell in which the plasmid has stably integrated into the ribosomal DNA genome and the transformed yeast cells in which the plasmid has not integrated into the ribosomal DNA genome with the agent under conditions suitable for growth, to produce a test yeast cell in which the plasmid has stably integrated into the ribosomal DNA genome and a test yeast cell in which the plasmid has not integrated into the ribosomal DNA genome;
   d) assessing growth of the test yeast cell in which the plasmid has stably integrated into the ribosomal DNA genome and a test yeast cell in which the plasmid has not integrated into the genome; and
   e) comparing the growth of the test yeast cell in which the plasmid has stably integrated into the ribosomal DNA genome with the growth of the test yeast cell in which the plasmid has not integrated into the ribosomal DNA genome, wherein reduced growth of the test yeast cell in which the plasmid has not integrated into the ribosomal DNA genome compared to the growth of the test yeast cell in which the plasiid has stably integrated into the ribosomal DNA genome indicates that the agent inhibits the replication or accumulation of ribosomal DNA circles in a veast cell.

2. A method according to claim 1, wherein the marker gene is selected from the group consisting of: ADE2, URA3, LEU2, TRP1, HIS3 and LYS2.

3. A method according to claim 1, wherein the autonomously replicating sequence is a ribosomal DNA autonomously replicating sequence.

4. The method of claim 1, wherein the agent extends the lifespan of the yeast cell.

5. The method of claim 1, wherein the agent inhibits the replication or accumulation of ribosomal DNA circles in a yeast cell with a mutation in the SGS1 gene.

6. A method of identifying an agent which inhibits the replication or accumulation of ribosomal DNA circles in a mammalian cell, comprising the steps of:
   a) transforming a mammalian cell with a plasmid comprising a ribosomal DNA replication origin and a marker gene to produce a transformed mammalian cell;
   b) identifying a transformed mammalian cell in which the plasmid has stably integrated into the ribosomal DNA genome and a transformed mammalian cell in which the plasmid has not integrated into the ribosomal DNA genome;
   c) incubating the transformed mammalian cell in which the plasmid has stably integrated into the ribosomal DNA genome and the transformed mammalian cell in which the plasmid has not integrated into the ribosomal DNA genome with the agent under conditions suitable for growth, to produce a test mammalian cell in which the plasmid has stably integrated into the ribosomal DNA genome and a test mammalian cell in which the plasmid has not integrated into the ribosomal DNA genome;
   d) assessing an average number of population doublings of the test mammalian cell in which the plasmid has stably integrated into the ribosomal DNA genome and a test mammalian cell in which the plasmid has not integrated into the ribosomal DNA genome; and
   e) comparing the average number of population doublings of the test mammalian cells in which the plasmid has stably integrated into the ribosomal DNA genome with the average number of population doublings of the test mammalian cell in which the plasmid has not integrated into the ribosomal DNA genome, wherein an increased in the average number of population doublings of the test mammalian cell in which the plasmid has not integrated into the ribosomal DNA genome compared to the population doublings of the test mammalian cell in which the plasmid has integrated into the ribosomal DNA genome indicates that the agent inhibits the replication or accumulation of ribosomal DNA circles in a mammalian cell.

7. The method of claim 6, wherein the agent extends the lifespan of the mammalian cell.

8. A method of identifying an agent which inhibits the formation of ribosomal DNA circles in a yeast cell, comprising the steps of:
   a) transforming a yeast cell deficient in a gene encoding a protein necessary for growth with a plasmid comprising a ribosomal DNA autonomously replicating sequence and a marker gene encoding the protein necessary for growth, to produce a transformed yeast cell;
   b) identifying a transformed yeast cell in which the plasmid has stably integrated into the genome and a transformed yeast cell in which the plasmid has not integrated into the genome;
   c) incubating the transformed yeast cell in which the plasmid has stably integrated into the genome and a transformed yeast cell in which the plasmid has not integrated into the ribosomal DNA genome with the agent under conditions suitable for growth, to produce a test yeast cell in which the plasmid has stably integrated into the ribosomal DNA genome and a test yeast cell in which the plasmid has not integrated into the ribosomal DNA genome;
   d) assessing growth of the test yeast cell in which the plasmid has stably integrated into the ribosomal DNA genome and the test yeast cell in which the plasmid has not integrated into the ribosomal DNA genome; and
   e) comparing the growth of the test yeast cell in which the plasmid has stably integrated into the ribosomal DNA genome with the growth of the test yeast cell in which the plasmid has not integrated into the ribosomal DNA genome, wherein reduced growth of the test yeast cell in which the plasmid has not integrated into the ribosomal DNA genome compared to growth of the test yeast cell in which the plasmid has stably integrated into the ribosomal DNA genome indicates that the agent inhibits the formation of ribosomal DNA circles in a yeast cell.

9. A method according to claim 8, wherein the marker gene is selected from the group consisting of: ADE2, URA3, LEU2, TRP1, HIS3 and LYS2.

10. The method of claim 8, wherein the agent extends the lifespan of the yeast cell.

11. The method of claim 8, wherein the agent inhibits the formation of ribosomal DNA circles in a yeast cell with a mutation in the SGS1 gene.

12. A method of identifying an agent which inhibits the formation of ribosomal DNA circles in a mammalian cell, comprising the steps of:
   a) transforming a mammalian cell with a plasmid comprising a ribosomal DNA replication origin and a marker gene to produce a transformed mammalian cell;
   b) identifying a transformed mammalian cell in which the plasmid has stably integrated into the ribosomal DNA genome and a transformed mammalian cell in which the plasmid has not integrated into the ribosomal DNA genome;
   c) incubating the transformed mammalian cell in which the plasmid has stably integrated into the ribosomal DNA genome and the transformed mammalian cell in which the plasmid has not integrated into the ribosomal DNA genome with the agent under conditions suitable for growth, to produce a test mammalian cell in which the plasmid has stably integrated into the ribosomal DNA genome and a test mammalian cell in which the plasmid has not integrated into the ribosomal DNA genome;
   d) assessing an average number of population doublings of the test mammalian cell in which the plasmid has stably integrated into the ribosomal DNA genome and a test mammalian cell in which the plasmid has not integrated into the ribosomal DNA genome; and
   e) comparing the average number of population doublings of the test mammalian cells in which the plasmid has stably integrated into the ribosomal DNA genome with the average number of population doublings of the test mammalian cells in which the plasmid has not integrated into the ribosomal DNA genome, wherein an increase in the average number of population doublings of the test mammalian cell in which the plasmid has not integrated into the ribosomal DNA genome compared to the population doublings of the test mammalian cell in which the plasmid has integrated into the ribosomal DNA genome indicates that the agent inhibits the formation of ribosomal DNA circles in a mammalian cell.

13. The method of claim 12, wherein the agent extends the lifespan of the mammalian cell.

* * * * *